US 10,188,107 B2

(12) United States Patent
Groth et al.

(10) Patent No.: US 10,188,107 B2
(45) Date of Patent: Jan. 29, 2019

(54) SELECTIVE INHIBITION OF C4-PEP CARBOXYLASES

(71) Applicant: Heinrich Heine Universität Düsseldorf, Düsseldorf (DE)

(72) Inventors: Georg Groth, Jülich (DE); Judith Katharina Paulus, Düsseldorf (DE); Daniel Schlieper, Düsseldorf (DE); Peter Westhoff, Neuss (DE)

(73) Assignee: HEINRICH HEINE UNIVERSITAT DUSSELDORF (DE)

( * ) Notice: Subject to any disclaimer, the term of this patent is extended or adjusted under 35 U.S.C. 154(b) by 96 days.

(21) Appl. No.: 14/761,088

(22) PCT Filed: Jan. 16, 2014

(86) PCT No.: PCT/EP2014/050766
§ 371 (c)(1),
(2) Date: Jul. 15, 2015

(87) PCT Pub. No.: WO2014/111448
PCT Pub. Date: Jul. 24, 2014

(65) Prior Publication Data
US 2015/0366206 A1 Dec. 24, 2015

Related U.S. Application Data

(60) Provisional application No. 61/753,049, filed on Jan. 16, 2013.

(51) Int. Cl.
*A01N 43/90* (2006.01)
*A01N 31/16* (2006.01)
(Continued)

(52) U.S. Cl.
CPC ............. *A01N 43/90* (2013.01); *A01N 31/16* (2013.01); *A01N 35/04* (2013.01); *A01N 37/40* (2013.01);
(Continued)

(58) Field of Classification Search
None
See application file for complete search history.

(56) References Cited

U.S. PATENT DOCUMENTS 6,020,287 A * 2/2000 Brinker .................. A01N 25/28
504/206

FOREIGN PATENT DOCUMENTS

| JP | WO 2013093007 | * 6/2013 |
| WO | WO 99/54495 | 10/1999 |
| WO | WO 2013/093007 A1 | 6/2013 |

OTHER PUBLICATIONS

International Preliminary Report on Patentability issued in related International Patent Application No. PCT/EP2014/050766, dated Jul. 30, 2015.
(Continued)

*Primary Examiner* — Alton N Pryor
(74) *Attorney, Agent, or Firm* — J.A. Lindeman & Co., PLLC

(57) ABSTRACT

The present invention relates to the use of a compound, a salt or solvate thereof as C4 plant selective herbicide wherein said compound has a structure according to formula (I) wherein A is a cyclic alkyl, aryl, heterocycloalkyl, or heteroaryl group, and B is a cyclic alkyl, aryl, heterocycloalkyl, or heteroaryl group, and wherein $R^1$, $R^2$, $R^3$, $R^4$ and $R^5$ are, independently of each other H or an alkyl group, and wherein integer i is 0 or 1, preferably 1, and the bond (a) is a single or double bond, and wherein in case (a) is a double bond, n is 0 and X is O or S, and wherein in case (a) is a single bond n is 1, and X is H or an alkyl group, and wherein the bond (b) is a single or double bond, and wherein in case (b) is a double bond, m and p are 0, and wherein in case (b) is a single bond m and p are both 1, and/or according to formula (II) including tautomeric structures thereof, wherein $R^{01}$ and $R^{02}$ are independently of each other selected from the group consisting of H, OH, carboxylic acid, ester, alkyl, alkoxy and halogen, wherein $Y^1$ is selected from the group consisting of (S(=O)2), S(=O)) and (C(=O)), and wherein $Y^2$ is O, and wherein r is 0 or 1 and wherein in case r is 0, q and s are 1, and wherein in case r is 1, q and s are 0, and wherein $R^{01}$, $R^{02}$, $R^{04}$, $R^{05}$, $R^{06}$, $R^{07}$, $R^{04\#}$, $R^{05\#}$, $R^{06\#}$, $R^{07\#}$, $R^{09}$, $R^{010}$, $R^{011}$ and $R^{012}$ are independently of each other selected from the group consisting of H, OH, —SO3H, carboxylic acid, ester, alkyl, alkoxy and halogen, said compound being capable of binding to the malate binding site comprised by a phosphoenolpyruvate carboxylase from a C4 plant, thereby inhibiting said phosphoenolpyruvate carboxylase.

Figure 2:
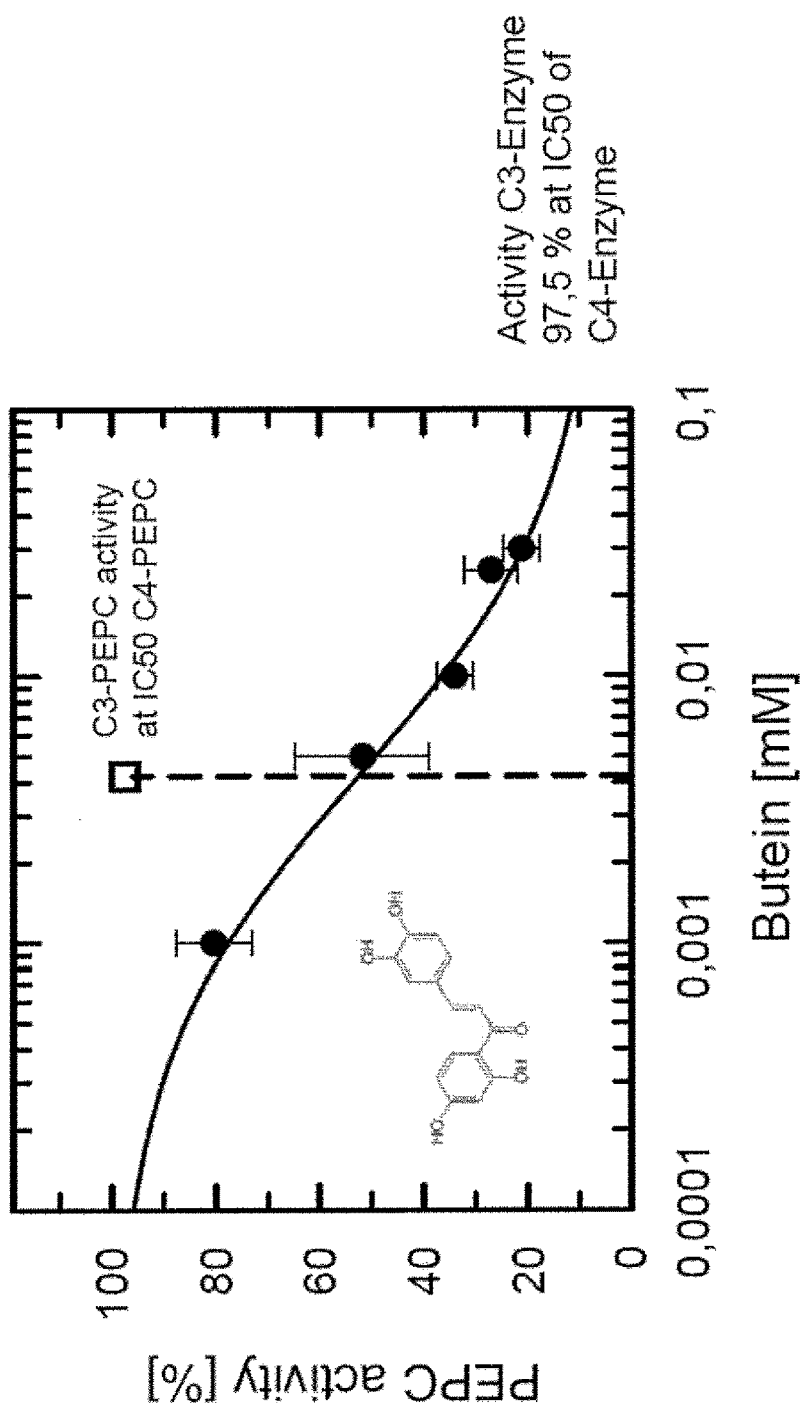

14 Claims, 8 Drawing Sheets
Specification includes a Sequence Listing.

(51) Int. Cl.
    A01N 35/04    (2006.01)
    A01N 37/40    (2006.01)
    A01N 43/26    (2006.01)
    A01N 43/30    (2006.01)
    A01N 43/32    (2006.01)
    A01N 43/16    (2006.01)
    A01N 43/60    (2006.01)
(52) U.S. Cl.
    CPC .............. A01N 43/16 (2013.01); A01N 43/26 (2013.01); A01N 43/30 (2013.01); A01N 43/32 (2013.01); A01N 43/60 (2013.01)

(56) References Cited

OTHER PUBLICATIONS

Higgins et al., Fast and sensitive multiple sequence alignments on a microcomputer, CABIOS, vol. 5, No. 2, pp. 151-153 (1989).
DeLano, "PyMOL: An Open-Source Molecular Graphics Tool," 9 pages (2002).
The CCP4 Suite: Programs for Protein Crystallography, "Collaborative Computational Project," No. 4, Acta. Cryst. D50, pp. 760-763 (1994).
Wang et al., "Identification of some novel AHAS inhibitors via molecular docking and virtual screening approach" Bioorganic & Medicinal Chemistry, vol. 15, No. 1; pp. 374-380 (2006).
Voigt, et al., "Comparison of the NCI Open Database with Seven Large Chemical Structural Databases," J. Chem. Inf. Comput. Sci., 41(3), 702-712 (2001).
Trott, et al., "AutoDock Vina: improving the speed and accuracy of docking with a new scoring function, efficient optimization and multithreading," Journ. of Computational Chemistry, vol. 31, pp. 455-461 (2010).
Strausberg, et al., "From Knowing to Controlling: A Path from Genomics to Drugs Using Small Molecule Probes," Science, vol. 300, pp. 294-295 (2003).
Rustin et al: "Fluorescence Study of Chemical Modification of Phosphoenolpyruvate Carboxylase from Crassula Argentea", Plant Physiol., pp. 1011-1016 (1991).
Mancera et al., "The molecular binding interactions of inhibitors and activators of phosphoenolpyruvate carboxylase" Journal of Molecular Structure; vol. 755, No. 1-3; pp. 151-159 (2005).
Miriam Lopez-Ramos et al: "HPPD: Ligand- and Target-based virtual Screening on a herbicide target"; Journal of Chemical Information and Model.; vol. 50, No. 5; May 24, 2010; pp. 801-814.
Hu et al: "Synthesis and herbicidal activities of novel 4-(4-(5-methyl-3-arylisoxazol-4-yl)thiazol-2-yl)piperidyl carboxamides and thiocarboxamides" Molecules, Molecular Diversity Presentation International, vol. 14, No. 3, Mar. 24, 2009; pp. 1288-1303.
Emsley et al., "Coot: Model-building Tools for Molecular Graphics," Acta Cryst. D60, pp. 2126-2132 (2004).
Kabsch, "Biological Crystallography", Acta Cryst., D66, pp. 125-132 (2010).
Harold Brown et al: "Assessing the Degree of C4 Photosynthesis in C3-C4 Species using an Inhibitor of Phosphoenolpyruvate Carboxylase" Plant Physiol.; Jan. 1, 1991, pp. 985-989.
Goto et al., "LIGAND: database of chemical compounds and reactions in biological pathways," M. Nucleic Acids Res., vol. 30, No. 1, 402-404 (2002).
Sascha Engelmann et al: "Molecular evolution of C4 phosphoenolpyruvate carboxylase in the genus Flaveria—a gradual increase from C3 to C4 characteristics," PLANTA, vol. 217, No. 5, pp. 717-725 (2003).
Durrant, et al., "AutoGrow: A Novel Algorithm for Protein Inhibitor Design," Chemical Biology & Drug Design, vol. 73, No. 2, pp. 168-178 (2009).
Crétin C et al: "Study on plant phosphoenolpyruvate carboxylases: sensitivity to herbicides and immunochemical reactivity", Physiologie Vegetale, Uthier-Villars, Paris, GA, vol. 21, Jan. 1, 1983, pp. 927-933.
Cooper, "Label-free screening of bio-molecular interactions," Anal. Bioanal. Chem., vol. 377, pp. 834-842 (2003).
Chaires, "Calorimetry and Thermodynamics in Drug Design," Annu. Rev. Biophys., vol. 37, pp. 135-151 (2008).
Cretin et al., "Differential Inhibition of Phosphoenol-Pyruvate Carboxylases by 2,4-Dichlorophenoxyacetic Acid and Two Newly Synthesized Herbicides," Phytochemistry, vol. 22, No. 12, pp. 2661-2664 (1983).
Jacobs et al., "Evolution of $C_4$ phosphoenolpyruvate carboxylase in Flaveria: determinants for high tolerance towards the inhibitor L-malate," Plant Cell and Environ., vol. 31, pp. 793-803 (2008).
Matsumura et al., "Crystal Structures of C4 Form Maize and Quaternary Complex of E. coli Phosphoenolpyruvate Carboxylases," Structure, vol. 10, pp. 1721-1730 (2002).
Pairoba et al., "Flavonoids as Inhibitors of NADP-Malic Enzyme and PEP Carboxylase from $C_4$ Plants," Biosci. Biotech. Biochem., vol. 60, No. 5, pp. 779-783 (1996).
Doyle et al., "A Rapid Screening Method to Detect Specific Inhibitors of Pyruvate Orthophosphate Dikinase as Leads for C4 Plant-Selective Herbicides," Journ. of Biomolecular Screening, vol. 10, No. 1, pp. 67-75 (2005).
Mancera et al,. "Quantitaive Structure—Activity Relationships of Competitive Inhibitors of Phosphoenolpyruvate Carboxylase," Bioorganic & Medicinal Chemistry, vol. 3, No. 3, pp. 217-225 (1995).
McFadden et al., "Potential Inhibitors of Phosphoenolpyruvate Carboxylase. II* Phosphonic Acid Substrate Analogues Derived from Reaction of Trialkyl Phosphites with Halomethacrylates," Aust. J. Chem., vol. 42, pp. 301-314 (1989).
Jenkins et al., "Effects of the Phosphoenolypyruvate Carboxylaste Inhibitor 3,3-Dichloro-2-(Dihydroxyphosphinoylmethyl)propenoate on Photosynthesis," Plant Physiol., vol. 89, pp. 1231-1237 (1989).
Jenkins et al., "3,3-Dichloro-2-Dihydroxyphosphinoylmethy1-2-Propenoate, a new, Specific Inhibitor of Phosphoenolpyruvate Carboxylase," vol. 14, No. 2, pp. 219-226 (1987).
Motti et al., "Screening Marine Fungi for Inhibitors of the C4 Plant Enzyme Pyruvate Phosphate Dikinase: Unguinol as a Potential Novel Herbicide Candidate," Applied and Environ. Microbiology, pp. 1921-1927 (2007).
Needleman et al., "A General Method Applicable to the Search for Similarities in the Amino Acid Sequence of Two Proteins," J. Mol. Biol., vol. 48, pp. 443-453 (1970).
Smith, "Comparison of Biosequences," Advances in Applied Mathematics, vol. 2, pp. 482-489 (1981).
Madhusudana et al., Herbricide-inhibited Phosphoenolpyruvate Carboxylase in Leaves of six Nonsucculent Scrub Species, Z. Pflanzenphysiol. Bd., vol. 99, pp. 69-74 (1980).
Paulus et al., "Evolution of C4 Phosphoenolypyruvate Carboxylase: Enhanced Feedback Inhibitor Tolerance is Determined by a Single Residue," Molecular Plant, vol. 6, No. 6, pp. 1996-1999 (2013).
[Abstract] Phosphoenolypyruvate carboxylase [Flaveria trinervia], Besnard et al., FEBS Lett. 292 (1-2) (1991).
[Abstract] Phosphoenolypyruvate carboxylase [Flaveria pringlei], Hermans et al., Mol. Gen. Genet. 234 (2), pp. 275-284 (1992).
[Abstract] Phosphoenolypyruvate carboxylase [Flaveria pringlei], Blaesing, Euro. J. Biochem. 246 (2), pp. 452-460 (1997).
Wolf, Digital Briefs, Science & Technology, Jul. 13, 2009, p. 31.
International Search Report and Written Opinion issued in related U.S. Patent Application No. PCT/EP2014/050766, completed Feb. 19, 2014.

* cited by examiner

Fig. 1

C3-Type

```
                              884
F_pringlei           PYLKQRIRLRDSYITTLNVCQAYTLKRIRDPNY (SEQ ID NO: 7)
Hordeum_vulgare      PYLKQRLRLRDPYITTLNVCQAYTLKRIRDPSF (SEQ ID NO: 3)
Oryza_sativa         LYLKQRLRLRNAYITTLNVCQAYTMKRIRDPDY (SEQ ID NO: 4)
ssp._indica
Triticum_aestiv      PYLKQRLRLRDAYITTMNVCQAYTLKRIRDPDY (SEQ ID NO: 5)
A_thaliana           PYLKQRLRLRDSYITTLNVCQAYTLKRIRDANY (SEQ ID NO: 6)
```

C4-Type

```
                              884
F_trinervia          PYLKQGIRLRDPYITTLNVCQAYTLKRIRDPNY (SEQ ID NO: 8)
F_australasica       PYLKQGIRLRDPYITTLNVCQAYTLKRIRDPNY (SEQ ID NO: 9)
Zea_mays             PFLKQGLVLRNPYITTLNVFQAYTLKRIRDPNF (SEQ ID NO: 10)
Sorghum_bicolor      PYLKQGLRLRNPYITTLNVFQAYTLKRIRDPSF (SEQ ID NO: 11)
Saccharum_spont      PYLKQGLRLRNPYITTLNVLQAYTLKRIRDPSF (SEQ ID NO: 12)
Saccharum_offic      PYLKQGLRLRNPYITTLNVLQAYTLKRIRDPCF (SEQ ID NO: 13)
```

C4-type PEPC R884Q     C4-type PEPC R884S     C4-type PEPC R884E

SELECTIVE INHIBITION OF C4-PEP CARBOXYLASES

In the past several different targets for selective and non-selective herbicides were identified. However, there still is a great need for new herbicides, especially selective herbicides. In particular specific herbicides against C4 plants would be of outmost importance for the agribusiness and a major turning point in the control of the worst weeds in the world. These weeds reduce the crop yield of the most important C3 cereals such as rice, wheat, barley and oat.

The C4 metabolism offers three potential targets for a selective herbicide. The first target is the enzyme phosphoenol pyruvate (PEP) carboxylase, which has a role in $CO_2$ fixation. The second target is the malic enzyme (ME) or the enzyme PEP carboxykinase (PEP CK) which catalyze the release of carbon dioxide in the bundle sheath cells. The third target is the enzyme pyruvate phosphate dikinase (PPDK), which regenerates PEP.

The substances unguinol and ilimaquinone were identified as selective inhibitors of PPDK from C4 plants maize, millet and proso millet. These substances were isolated from marine organisms (Motti et al., 2007). The only universal target, that is common to all variants of C4 metabolism, is the enzyme PEP carboxylase. Due to the high sequence homology between the C4 specific PEP carboxylase and the C3 isoforms, which have further roles in the general C3 metabolism in plants and other organism, it is not obvious to use this enzyme as selective target.

The PEP carboxylase inhibitors described so far (Jenkins et al., 1987; Jenkins, 1989; McFadden et al., 1989; Mancera et al., 1995) are based on PEP analogues (e. g., 3,3-Dichloro-2-(dihydroxyphosphinoylmethyl) propenoate (DCDP)). However, these compounds also inhibit C3 type PEP carboxylases at rates between 12-46% (Jenkins, 1989) and do not inhibit growth of C4 plants (Doyle et al., 2005). Pairoba et al. (1996) showed that PEP carboxylase from C4 plant *Amaranthus viridis* is inhibited by several flavonoles and flavones. The inhibiting flavonoles are quercetin, quercitrin, rutin, kaempferol, fisetin, morin, and myricetin. The inhibiting flavone was baicalein/baicalin. But in that work, neither the binding site of the inhibiting flavonoles (or flavones, resp.), nor the molecular mechanism of inhibition were identified. Thus, the mechanism of the inhibiting flavonoles and flavones is unknown. Furthermore, the substances were also described as inhibitors of the malic enzyme from *A. viridis*, a fact that implies a fairly unspecific inhibition. Furthermore, the authors failed to show that the tested flavonoles and flavones inhibit C4 type PEP carboxylases only, but not C3 type isoforms.

The crystal structures of PEP carboxylase from *Escherichia coli* (C3 type) and from the C4 plant maize are known (Matsumura et al., 2002). In the publications of these structures, several amino acid side chains were identified as important for the binding of the feedback inhibitors malate and aspartate. However, the authors failed to note the structural difference of the malate binding site that we use in the development of C4 selective herbicides.

Thus, there is a need for effective C4 specific herbicides for all-purpose use, since no selective inhibitors of PEP carboxylase from C4 plants are known.

As set forth above, ilimaquinone and unguinol were identified as inhibitors of PPDK. These inhibitors, however, have several disadvantages, since they inhibit a subgroup of C4 plants. Tropical grasses, which use PEP carboxykinase for $CO_2$ release and PEP regeneration, are not inhibited. Further, the inhibitors need complex biosynthesis pathways and are expensive to produce (100 μg ilimanquinone cost 150 Euro). Also, both compounds have a low solubility in water (high clog values), which hampers the resorption by the plants.

Moreover, the inhibitory concentration of the compounds is high and they show poor solubility (unguinol ClogP=5.7 and ilimaquinone ClogP=6.0). The half maximal inhibitory concentration (IC50) is 40 μM for unguinol and 292 μM for ilimanquinone for the isolated enzyme (Motti et al. 2007). Therefore, an inhibition of the plant would need much higher concentrations up to millimolar range. Due to the high production costs, the use of these compounds is not economical.

Finally, unguinol is used as growth hormone for animals, has anti-microbial and cytotoxic activity and inhibits the enzyme bile salt hydrolase. Therefore, it is unsuitable as herbicide.

For those flavonoles and flavones that were identified as inhibitors of PEP carboxylase from C4 plant *A. viridis*, the control experiments with C3 plants are missing to show the selective inhibition of the C4 isoform. The title of the publication suggests inhibitory effect of the complete group of flavonoids (Pairoba et al., 1996), but the authors failed to show this claim. Flavonoids are with approx. 7000 different substances the largest class of plant secondary metabolites and have a high structural diversity. From this structurally heterogeneous class of substances, only a few flavonoles and flavones were tested. Flavanones, flavandioles, flavanes, flavanoles, isoflavones and anthocyanes, which also belong to the flavanoides, were not tested.

Furthermore, an inherent disadvantage of naturally occurring flavonoids is their low solubility in water, impeding the application as well the resorption of these substances.

The inherent disadvantage of all tested PEP analogues is the fact that they also inhibit C3 type PEP carboxylases to a certain degree. They do not show any effect on the growth of C4 plants.

Thus, there is a need for effective C4 selective inhibitors. Thus, the present invention relates to use of at least one compound, salt or solvate thereof, preferably of a compound, salt or solvate thereof, as C4 plant selective herbicide, wherein said compound has a structure according to formula (I)

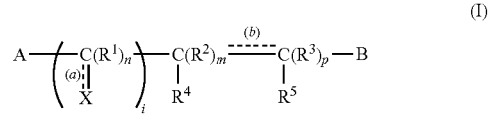

wherein A is a cyclic alkyl, aryl, heterocycloalkyl, or heteroaryl group, and B is a cyclic alkyl, aryl, heterocycloalkyl, or heteroaryl group, and wherein $R^1$, $R^2$, $R^3$, $R^4$ and $R^5$ are, independently of each other H or an alkyl group, and the bond (a) is a single or double bond, and wherein integer i is 0 or 1, and wherein in case (a) is a double bond, n is 0 and X is O or S, and wherein in case (a) is a single bond n is 1, and X is H or an alkyl group, and wherein the bond (b) is a single or double bond, and wherein in case (b) is a double bond, m and p are 0, and wherein in case (b) is a single bond m and p are both 1, and/or according to formula (II)

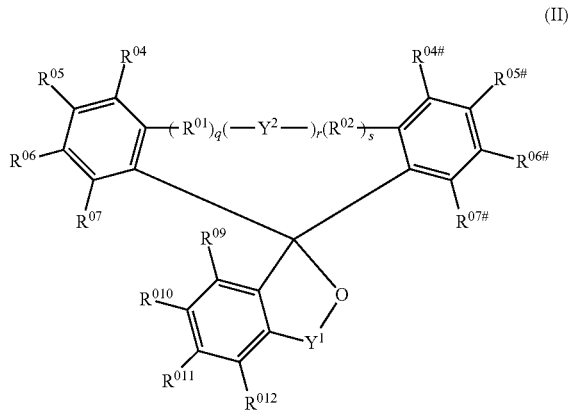

(II)

including tautomeric structures thereof, wherein $R^{O1}$ and $R^{O2}$ are independently of each other selected from the group consisting of H, OH, carboxylic acid, ester, alkyl, alkoxy and halogen, wherein $Y^1$ is selected from the group consisting of (S(=O)2), S(=O)) and (C(=O)), and wherein $Y^2$ is O, and wherein r is 0 or 1 and wherein in case r is 0, q and s are 1, and wherein in case r is 1, q and s are 0, and wherein $R^{O1}$, $R^{O2}$, $R^{O4}$, $R^{O5}$, $R^{O6}$, $R^{O7}$, $R^{O4\#}$, $R^{O5\#}$, $R^{O6\#}$, $R^{O7\#}$, $R^{O9}$, $R^{O10}$, $R^{O11}$ and $R^{O12}$ are independently of each other selected from the group consisting of H, —OH, —SO$_3$H, carboxylic acid, ester, alkyl, alkoxy and halogen, said compound being capable of binding to the malate binding site comprised by a phosphoenolpyruvate carboxylase from a C4 plant, thereby inhibiting said phosphoenolpyruvate carboxylase.

It is to be understood that also mixtures of two or more of the above mentioned compounds may be used as C4 inhibitors, thus mixtures of two or more compounds according to formula (I) or mixtures of two or more compounds according to formula (II) or mixtures of at least one compound according to formula (I) and at least one compound according to formula (II).

Within the meaning of the present invention, the term "alkyl" relates to non-branched alkyl residues and branched alkyl residues, as well as residues comprising one or more heteroatoms or functional groups, such as, by way of example, —O—, —S—, —NH—, —NH—C(=O)—, —C(=O)—NH—, and the like. The term also encompasses alkyl groups which are further substituted by one or more suitable substituent.

Within the meaning of the present invention, the term "cyclic alkyl" or "cycloalkyl" relates to optionally suitably substituted 4 to 8-membered single-ring alkyl groups as well as optionally suitably substituted multicyclic alkyl residues.

Within the meaning of the present invention, the term "heterocycloalkyl" relates to optionally suitably substituted 4 to 8-membered single-ring alkyl groups as well as optionally suitably substituted multicyclic alkyl residues comprising one or more, preferably from 1 to 4 such as 1, 2, 3 or 4, heteroatoms, wherein in case the cycloalkyl residue comprises more than 1 heteroatom, the heteroatoms may be the same or different.

The term "alkyl", "cycloalkyl", "cyclic alkyl" and "heterocycloalkyl", also encompasses groups which are further substituted by one or more suitable substituent.

The term "substituted" as used in this context of the present invention preferably refers to alkyl, cycloalkyl, cyclic alkyl, aryl, heteroaryl and heterocycloalkyl groups being substituted in any position by one or more substituents, preferably by 1, 2, 3, 4, 5 or 6 substituents, more preferably by 1, 2, or 3 substituents. If two or more substituents are present, each substituent may be the same or may be different from the at least one other substituent. There are in general no limitations as to the substituent.

The substituents may be, for example, selected from the group consisting of aryl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, amino, acylamino, including alkylcarbonylamino, arylcarbonylamino, carbamoyl and ureido, amidino, nitro, imino, sulfhydryl, alkylthio, arylthio, thiocarboxylate, sulfates, alkylsulfinyl, sulfonate, sulfamoyl, sulfonamido, trifluoromethyl, cyano, azido, cycloalkyl such as e.g. cyclopentyl or cyclohexyl, heterocycloalkyl such as e.g. morpholino, piperazinyl or piperidinyl, alkylaryl, arylalkyl and heteroaryl. Preferred substituents of such organic residues are, for example, halogens, such as fluorine, chlorine, bromine or iodine, amino groups, hydroxyl groups, carbonyl groups, thiol groups and carboxyl groups.

Preferred examples for cycloalkyl groups are, e.g., cyclopentyl or cyclohexyl or stereoids, such as, e.g., steroids having a pregnane skeleton, such as 12,20-dioxypregnane-3-yl.

Preferred examples for heterocycloalkyl groups are, e.g., morpholino, piperazinyl or piperidinyl.

Within the meaning of the present invention, the term "aryl" refers to, but is not limited to, optionally suitably substituted 5- and 6-membered single-ring aromatic groups as well as optionally suitably substituted multicyclic groups, for example bicyclic or tricyclic aryl groups. The term "aryl" thus includes, for example, optionally substituted phenyl groups or optionally suitably substituted naphthyl groups. Aryl groups can also be fused or bridged with alicyclic or heterocycloalkyl rings are not aromatic so as to form a polycycle, e.g., benzodioxolyl or tetraline. The term "aryl" further includes aromatic groups which linked via a single bond to further aromatic groups so as to form, e.g., biphenyl groups.

The term "heteroaryl" as used within the meaning of the present invention includes optionally suitably substituted 5- and 6-membered single-ring aromatic groups as well as substituted or unsubstituted multicyclic aryl groups, for example bicyclic or tricyclic aryl groups, comprising one or more, preferably from 1 to 4 such as 1, 2, 3 or 4, heteroatoms, wherein in case the aryl residue comprises more than 1 heteroatom, the heteroatoms may be the same or different. Such heteroaryl groups including from 1 to 4 heteroatoms are, for example, benzodioxolyl, pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzoimidazolyl, benzothiophenyl, methylenedioxyphenylyl, napthyridinyl, quinolinyl, isoquinolinyl, indolyl, isoindolyl, benzofuranyl, purinyl, deazapurinyl, pteridinyl, or indolizinyl.

The term "substituted aryl" and the term "substituted heteroaryl" as used in the context of the present invention describes moieties having substituents replacing a hydrogen on one or more atoms, e.g. C or N, of an aryl or heteroaryl moiety. Again, there are in general no limitations as to the substituent. The substituents may be, for example, selected from the group consisting of alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxy, phosphate, phosphonato, phosphinato, amino, acylamino, including alkylcarbonylamino, arylcarbonylamino, carbamoyl and ureido, amidino, nitro, imino, sulfhydryl, alkylthio, arylthio, thiocarboxylate, sulfates, alkylsulfinyl, sulfonate, sulfamoyl, sulfonamido, trifluoromethyl, cyano, azido, cycloalkyl such as e.g. cyclopentyl or cyclohexyl, heterocycloalkyl such as e.g. morpholino, piperazinyl or piperidinyl, alkylaryl, arylalkyl and heteroaryl.

Preferred substituents of such organic residues are, for example, halogens, such as fluorine, chlorine, bromine or iodine, amino groups, hydroxyl groups, carbonyl groups, thiol groups, amino groups, and carboxyl groups.

Thus, the cyclic alkyl (cycloalkyl), heterocycloalkyl, aryl or heteroaryl group is, e.g., selected from the group consisting of, optionally suitably substituted, benzodioxolyl, pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzoimidazolyl, benzothiophenyl, methylenedioxyphenylyl, napthyridinyl, quinolinyl, isoquinolinyl, indolyl, isoindolyl, benzofuranyl, purinyl, deazapurinyl, pteridinyl, indolizinyl, phenyl, biphenyl and stereoids.

The Compounds According General Formula (I)

According to a first preferred embodiment, the present invention relates to a use of a compound a salt or solvate thereof as C4 plant selective herbicide wherein said compound comprises a cyclic alkyl, aryl, heterocycloalkyl or heteroaryl group, wherein the compound has a structure according a structure according to formula (I)

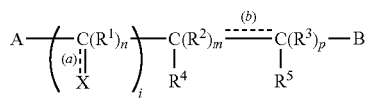

wherein A is a cyclic alkyl, aryl, heterocycloalkyl, or heteroaryl group, and B is a cyclic alkyl, aryl, heterocycloalkyl, or heteroaryl group,
and wherein $R^1$, $R^2$, $R^3$ $R^4$ and $R^5$ are, independently of each other H or an alkyl group,
wherein integer i is 0 or 1,
and the bond (a) is a single or double bond,
and wherein in case (a) is a double bond, n is 0 and X is O or S, and wherein in case (a) is a single bond n is 1, and X is H or an alkyl group,
and wherein the bond (b) is a single or double bond, and
  wherein in case (b) is a double bond, m and p are 0, and
  wherein in case (b) is a single bond m and p are both 1,
said compound being capable of binding to the malate binding site comprised by a phosphoenolpyruvate carboxylase from a C4 plant, thereby inhibiting said phosphoenolpyruvate carboxylase.

It is contemplated that the binding to the malate binding site of a phosphoenolpyruvate carboxylase from a C3 plant is inhibited by steric or electrostatic constraints of a conserved arginine in the binding site of the C3 PEPC (Arg-884 in *Flaveria pringlei*).

Thus, the present invention also relates to the use of a compound of formula (I) as described above, wherein binding to the malate binding site of a phosphoenolpyruvate carboxylase from a C3 plant is inhibited by steric or electrostatic constraints of a conserved arginine in the binding site of the C3 PEPC, preferably by Arg-884 in *Flaveria pringlei*. The amino acid sequence of the C3 PEPC of *Flaveria pringlei* is shown in SEQ ID NO: 2. The sequence can be also found in GenBank, see GenBank Accession number GenBank: CAA88829.1 GI:763097).

Preferably i is 1 and the compound has the structure

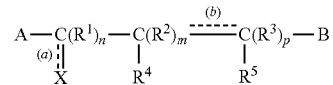

According an alternative embodiment i is 0, and the compound has the structure

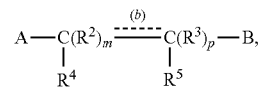

in particular wherein

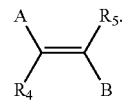

Residue A

A is selected from the group consisting of cyclic alkyl, aryl, heterocycloalkyl and heteroaryl group. As described above, the terms cyclic alkyl, aryl, heterocycloalkyl and heteroaryl group may be substituted or unsubstituted. Thus, A is selected from the group consisting of unsubstituted cyclic alkyl, unsubstituted aryl, unsubstituted heterocycloalkyl, unsubstituted heteroaryl group, substituted cyclic alkyl, substituted aryl, substituted heterocycloalkyl and substituted heteroaryl group.

Preferably, A is a substituted or unsubstituted phenyl, benzodioxolyl or benzodioxinyl group.

In particular A is

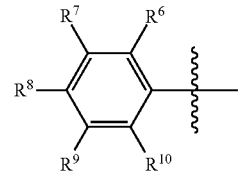

wherein $R^6$, $R^7$, $R^8$, $R^9$ and $R^{10}$ are, independently of each other, selected from the group consisting of H, OH, carboxylic acid, ester, alkyl, alkoxy and halogen or wherein two residues in ortho position to each other form a cyclic or heterocyclic ring. The term "wherein two residues in ortho position to each other form a cyclic or heterocyclic ring" refers to such residues as $R^6$ and $R^7$, or $R^7$ and $R^8$, or $R^8$ and $R^9$, or $R^9$ and $R^{10}$. In case two residues in ortho position to each other form a cyclic or heterocyclic ring, preferably $R^7$ and $R^8$ or $R^8$ and $R^9$ form a ring.

Preferably, $R^6$, $R^7$, $R^8$, $R^9$ and $R^{10}$ are, independently of each other, selected from the group consisting of H, OH, —COOH, —C(=O)-alkyl, —O-alkyl, alkyl, Cl, Br and I, wherein alkyl is in particular methyl or ethyl, in particular methyl.

The following preferred groups A are mentioned by way of example:

TABLE 1

| | | | | |
|---|---|---|---|---|
| $R^6$ | $R^7$ | $R^8$ | $R^9$ | $R^{10}$ |
| Selected from the group consisting of H, OH, —COOH, —C(=O)—Me, —OMe, methyl, Cl, Br and I | H, OH | H, OH | H, OH | H; OH |
| H, OH | Selected from the group consisting of H, OH, —COOH, —C(=O)—Me, —OMe, methyl, Cl, Br and I | H, OH | H, OH | H, OH |
| H, OH | H, OH | Selected from the group consisting of H, OH, —COOH, —C(=O)—Me, —OMe, methyl, Cl, Br and I | H, OH | H, OH |

In particular A is selected from the group consisting of:

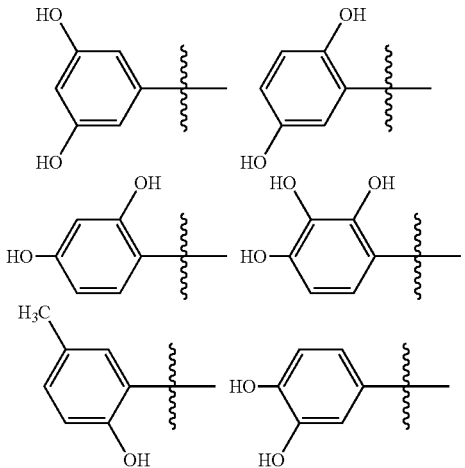

Residue B

B is selected from the group consisting of cyclic alkyl, aryl, heterocycloalkyl and heteroaryl group. As described above, the terms cyclic alkyl, aryl, heterocycloalkyl and heteroaryl group may be substituted or unsubstituted. Thus, B is selected from the group consisting of unsubstituted cyclic alkyl, unsubstituted aryl, unsubstituted heterocycloalkyl, unsubstituted heteroaryl group, substituted cyclic alkyl, substituted aryl, substituted heterocycloalkyl and substituted heteroaryl group.

Preferably, B is a substituted or unsubstituted phenyl, benzodioxolyl or benzodioxinyl group. In particular B is

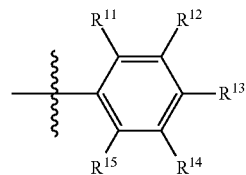

wherein $R^{11}$, $R^{12}$, $R^{13}$, $R^{14}$ and $R^{15}$ are, independently of each other, selected from the group consisting of H, OH, carboxylic acid, ester, alkyl, alkoxy and halogen, or wherein two residues in ortho position to each other form a cyclic or heterocyclic ring. The term "wherein two residues in ortho position to each other form a cyclic or heterocyclic ring" refers to such residues as $R^{11}$ and $R^{12}$, or $R^{12}$ and $R^{13}$, or $R^{13}$ and $R^{14}$, or $R^{14}$ and $R^{15}$. In case two residues in ortho position to each other form a cyclic or heterocyclic ring, preferably or $R^{12}$ and $R^{13}$ or $R^{13}$ and $R^{14}$ form a ring.

Preferably, $R^{11}$, $R^{12}$, $R^{13}$, $R^{14}$ and $R^{15}$ are, independently of each other, selected from the group consisting of H, OH, —COOH, —C(=O)-alkyl, —O-alkyl, alkyl, Cl, Br and I, or wherein two residues in ortho position to each other form together the group O—CH$_2$—O—, —O—CH$_2$—CH2-O—, wherein alkyl is in particular methyl or ethyl, in particular methyl.

The following preferred groups B are mentioned by way of example:

TABLE 2

| $R^{11}$ | $R^{12}$ | $R^{13}$ | $R^{14}$ | $R^{15}$ |
|---|---|---|---|---|
| Selected from the group consisting of H, OH, —COOH, —C(=O)—Me, —OMe, methyl, Cl, Br and I | H, OH | H, OH | H, OH | H; OH |
| H, OH | Selected from the group consisting of H, OH, —COOH, —C(=O)—Me, —OMe, methyl, Cl, Br and I | H, OH | H, OH | H, OH |
| H, OH | H, OH | Selected from the group consisting of H, OH, —COOH, —C(=O)—Me, —OMe, methyl, Cl, Br and I | H, OH | H, OH |
| H, OH | H, OH | —O—CH$_2$—O—, —O—CH$_2$—CH2-O— | | H, OH |

In particular B is selected from the group consisting of:

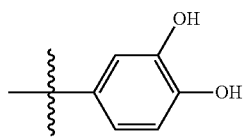

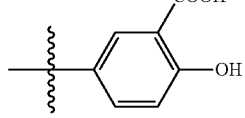

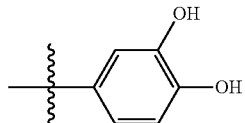

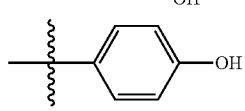

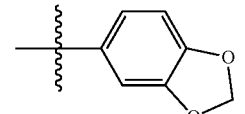

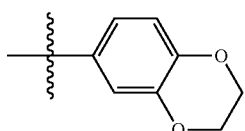

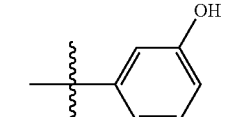

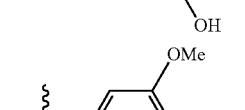

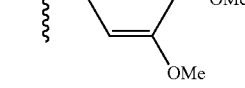

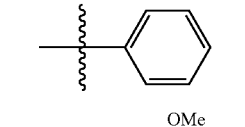

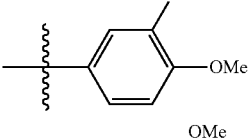

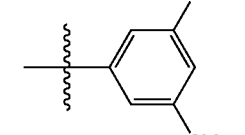

Preferably, integer n in formula (I) is 0 and (a) is a double bond. In this case, X is preferably O or S, in particular O.

Thus, the present invention also relates to the use of a compound, as described above, having the following structure:

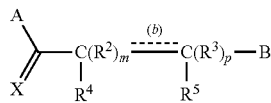

wherein X is preferably O or S, in particular O. More preferably the compound described above has the structure

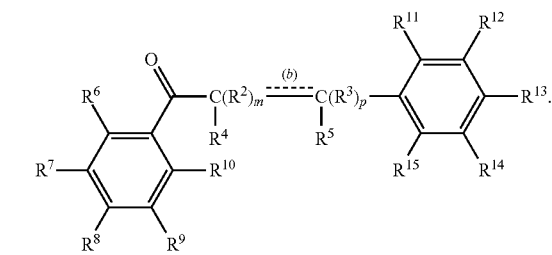

More preferably, (b) is a double bond and p is 0 and the compound has the structure

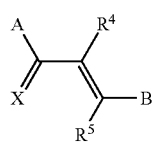

wherein X is preferably O or S, in particular O and with A and B, $R^4$ and $R^5$ being as described above.

Thus, the present invention also relates to the use of a compound as described above, having the structure

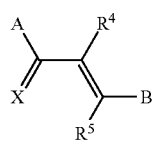

wherein X is preferably O or S, in particular O and with A and B, $R^4$ and $R^5$ being as described above, preferably with A being

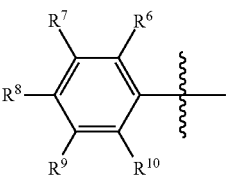

and/or B being
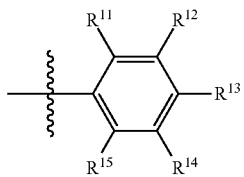
more preferably having the structure
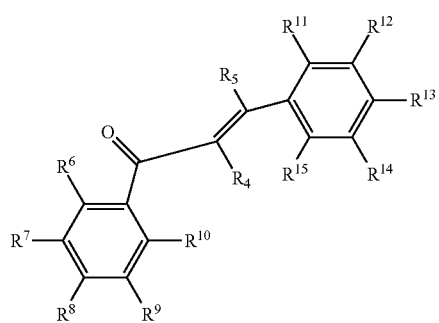
more preferably with A being selected from the group
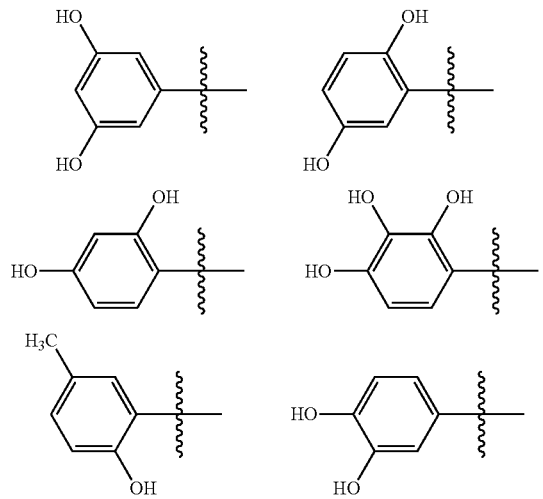
and/or B being selected from the group
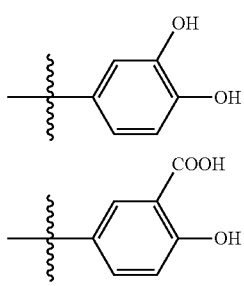
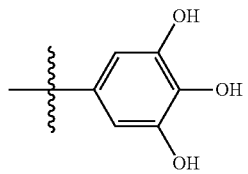
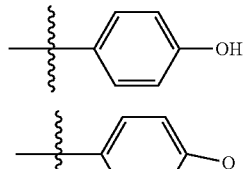
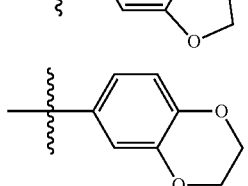
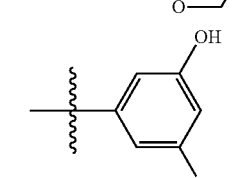
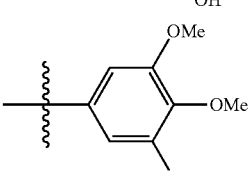
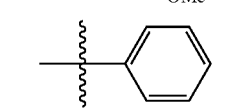
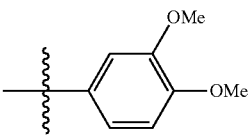
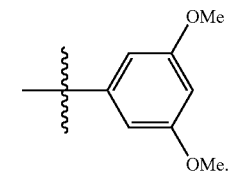
According to a further preferred embodiment, (b) is a single bond and the compound has the structure
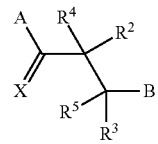
wherein X is preferably O or S, in particular O, and preferably with A being

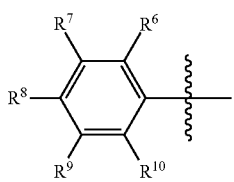

and/or B being

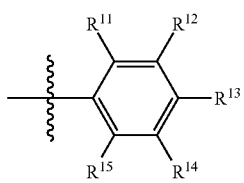

more preferably having the structure

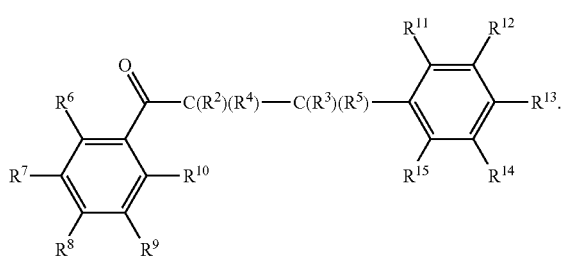

more preferably with A being selected from the group

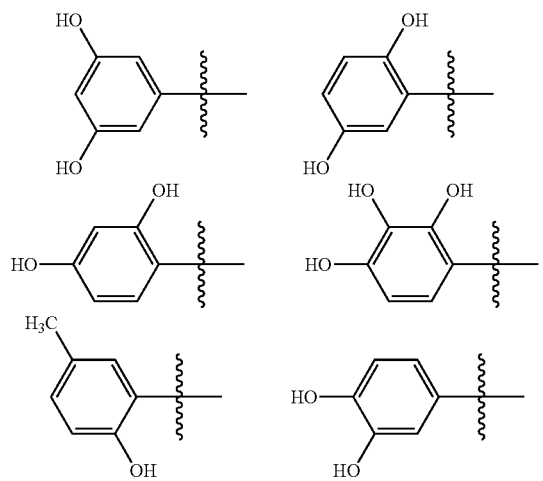

and/or B being selected from the group

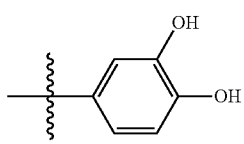

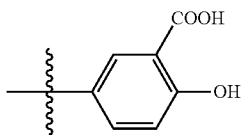

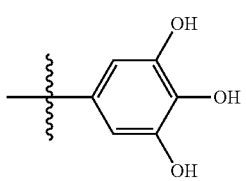

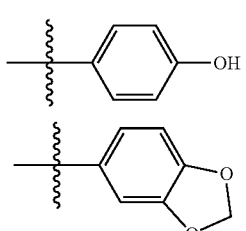

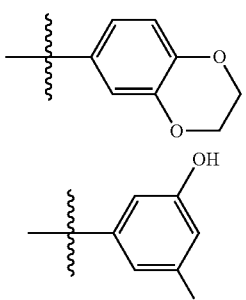

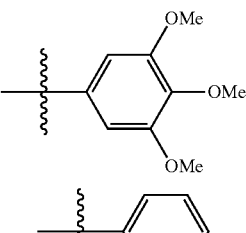

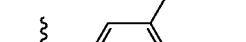

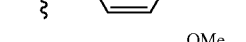

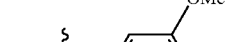

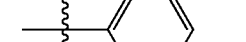

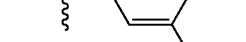

Most preferably in this case, R2 and R3 are independently of each other, selected from the group, H, methyl, ethyl, n-butyl, sec-butyl and tert-butyl, in particular both H.

According to a further preferred embodiment, wherein n in formula (I) is 1, (a) is a single bond and X is H or alkyl, the compound thus having preferably the following structure

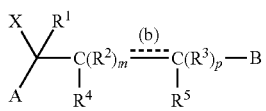

more preferably wherein the compound has the structure

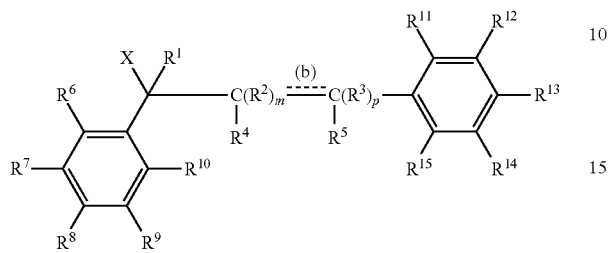

According to this embodiment, B is in particular a double bond and the compound has the structure

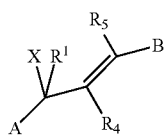

more preferably the structure

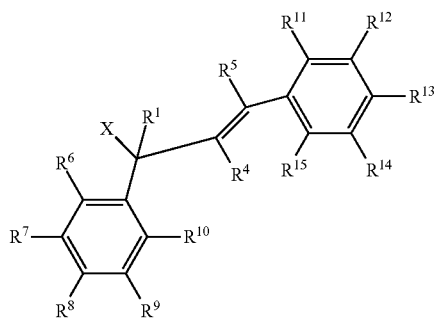

In case X is an alkyl group, X is preferably methyl, ethyl, n-butyl, sec-butyl or tert-butyl.

Residues $R^4$ and $R^5$

Residues $R^4$ and $R^5$ are preferably H or alkyl, more preferably, independently of each other, selected from the group, H, methyl, ethyl, n-butyl, sec-butyl and tert-butyl.

Most preferably, the compound, described above, is selected

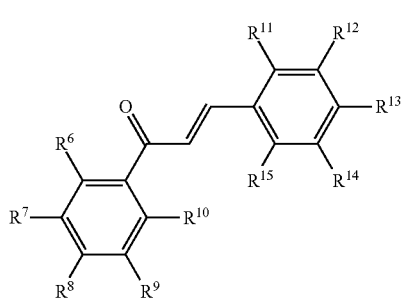

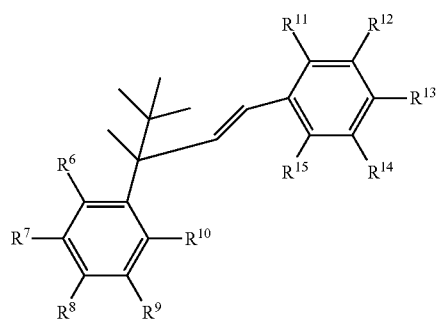

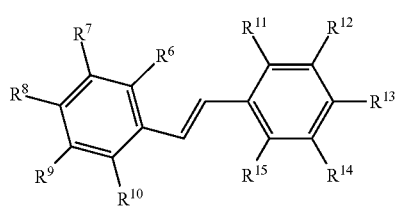

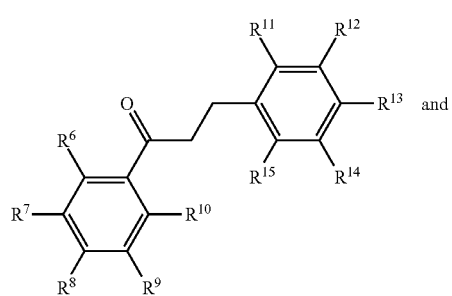 and

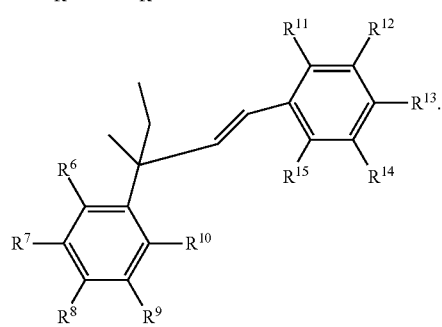

According to a particularly preferred embodiment, the compound is selected from the group consisting of butein, Piceatannol, trans-1-(3'-Carboxy-4'-hydroxyphenyl)-2-(2,5-dihydroxy-phenyl)ethane, Robtein, and Okanin, thus selected from the group consisting of

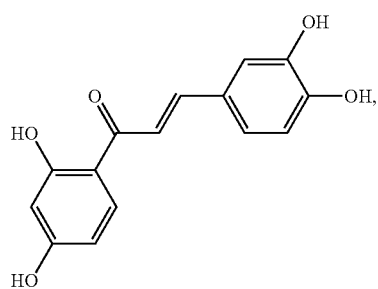

-continued

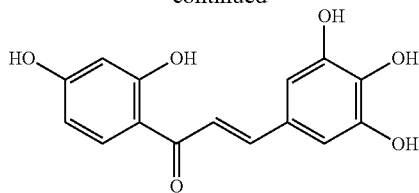

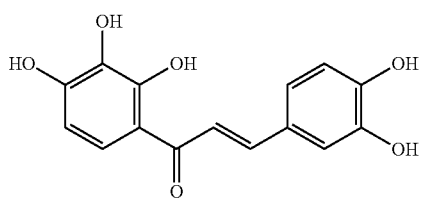

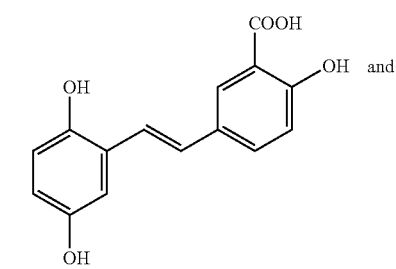

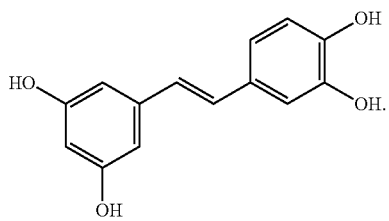

According to an alternative embodiment of the present invention, the compound has the structure (II)

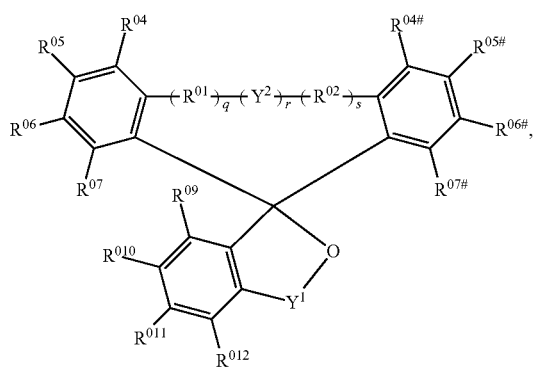

as described above or a tautomeric structure thereof. The term tautomeric structure is denoted to mean that at least one of residues $R^{01}$, $R^{02}$, $R^{04}$, $R^{05}$, $R^{06}$, $R^{07}$, $R^{04\#}$, $R^{05\#}$, $R^{06\#}$ or $R^{07\#}$ comprises a proton, such as is a OH group, and in the tautomeric dorm this H is attached to the O adjacent to Y1 to give ring opened structure:

Preferably, in formula (II) $Y^2$ is O, and r is 1. In this case, q and s are 0, and the compound has the structure

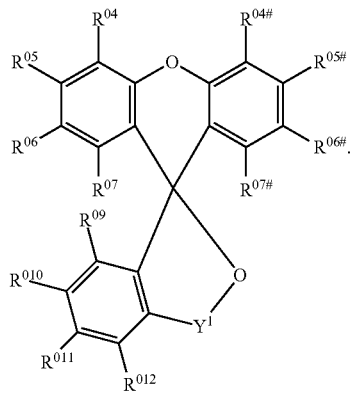

More preferably, r is 0 and wherein q and s are 1, the compound has the structure

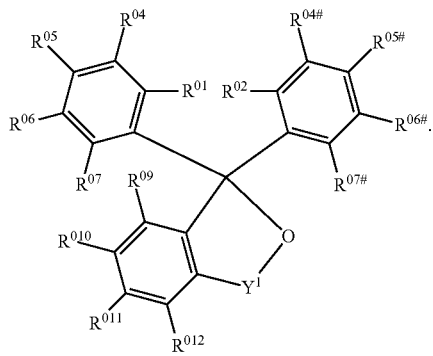

The Group $Y^1$

As described above, $Y^1$ is preferably selected from the group consisting of (S(=O)$_2$). S(=O)) and (C(=O)).

Thus, the present invention also relates to a use of a compound, as described above, the compound having a structure selected from the group consisting of

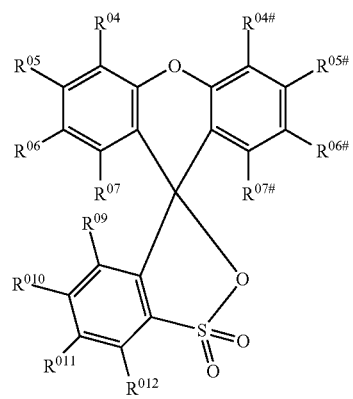

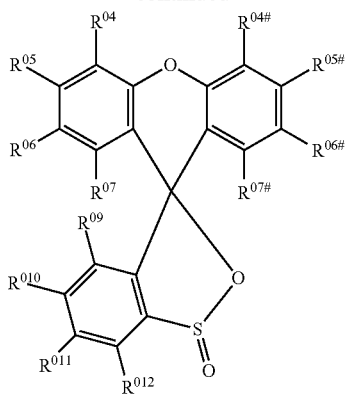

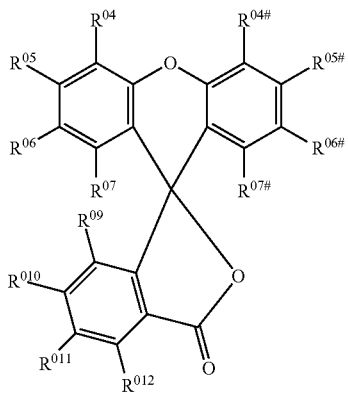

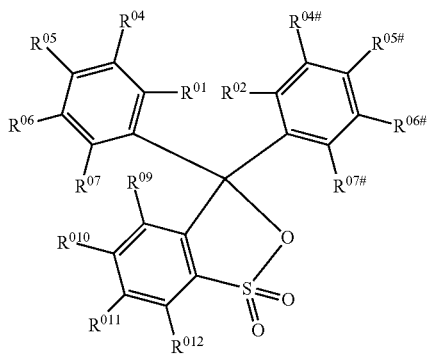

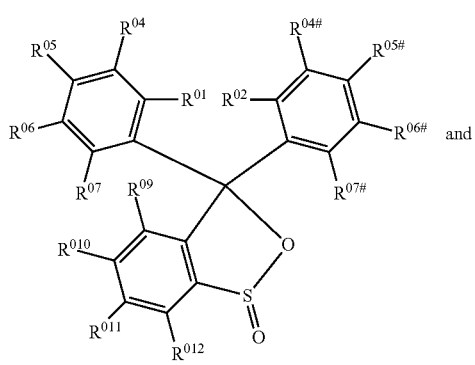

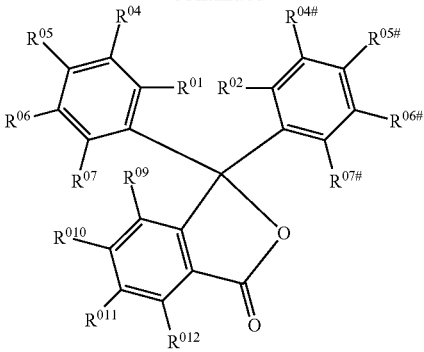

As described above, $R^{01}$, $R^{02}$, $R^{04}$, $R^{05}$, $R^{06}$, $R^{07}$, $R^{04\#}$, $R^{05\#}$, $R^{06\#}$, $R^{07\#}$, $R^{09}$, $R^{010}$, $R^{011}$ and $R^{012}$ are independently of each other selected from the group consisting of H, OH, —SO$_3$H, carboxylic acid, ester, alkyl, alkoxy and halogen. Preferably, $R^{01}$, $R^{02}$, $R^{04}$, $R^{05}$, $R^{06}$, $R^{07}$, $R^{04\#}$, $R^{05\#}$, $R^{06\#}$, $R^{07\#}$, $R^{09}$, $R^{010}$, $R^{011}$ and $R^{012}$ are independently of each other selected from the group consisting of H, OH, —COOH, —SO$_3$H, —C(=O)-alkyl, —O-alkyl, alkyl, Cl, Br and I, wherein alkyl is preferably methyl or ethyl.

Preferably, the compound is selected from the group consisting of Pyrocatechol Violet, Pyrogallol Red, Gallein, Chrome Cyanine R, Cresol Red, Chlorphenol Red, Sulfonfluorescein, BLAH (spiro[benzo[c][1,2]oxathiole-3,9'-xanthene]1-oxide), 9,9-bis(4-methoxyphenyl)-8-oxa-7{4}-thiabicyclo[4.3.0.0]nona-2,4,10-triene, 2-hydroxy-5-[3-(4-hydroxy-3-isopropyl-5-sulfo-phenyl)-1,1-dioxo-benzo[c]oxathiol-3-yl]-3-isopropyl-b, phenol red, chlorphenoly red, bromphenol red, bromochlorophenol blue, bromophenol blue, iodophenol blue, Pyrogallolsulfonphthalein, brompyrogallored, bromochlorophenol blue, bromopheno blue, iodphenol blue, kresol red, bromokresol red, kresolpurpur (m-Kresolsulfonphthalein), bromokresolpurpur, kresolpurpur, bromokresol green, thymol blue, bromothymol blue, xylenol blue, bromoxylenol blue Preferably, the compound is selected from the group consisting of Pyrocatechol Violet, Gallein, Chrome Cyanine R and Cresol Red.

According to one particularly preferred embodiment, $R^{05}$, $R^{06}$, $R^{05\#}$, $R^{06\#}$ are OH, more preferably the compound has the structure

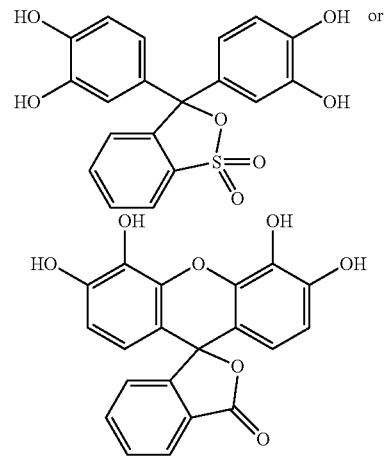

Suitable Salt

As described above, the compounds of the present invention can be formulated as suitable salt or solvate.

Typical acceptable salts include those salts prepared by reaction of the compounds of the present invention with an acceptable mineral or organic acid or an organic or inorganic base. Such salts are known as acid addition and base addition salts. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such suitable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, napthhalene-2-sulfonate, mandelate and the like. Preferred suitable acid addition salts are those formed with mineral acids such as hydrochloric acid and hydrobromic acid, and those formed with organic acids such as maleic acid and methanesulfonic acid. Salts of amine groups may also comprise quaternary ammonium salts in which the amino nitrogen carries a suitable organic group such as an alkyl, alkenyl, alkynyl, or aralkyl moiety. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counter ion forming a part of any salt of this invention is usually not of a critical nature, so long as the salt as a whole is suitable and as long as the counter ion does not contribute undesired qualities to the salt as a whole.

The term acceptable solvate encompasses also suitable solvates of the compounds of the invention, wherein the compound combines with a solvent such as water, methanol, ethanol, DMSO, acetonitrile or a mixture thereof to form a suitable solvate such as the corresponding hydrate, methanolate, ethanolate, DMSO solvate or acetonitrilate.

The compound of the present invention may be provided in form of an herbicide formulation. Accordingly, the compounds to be used in the context of the present invention can be formulated in a variety of ways. The following possibilities may be suitable for formulation: e.g. emulsifiable concentrates, emulsions, suspension concentrates, capsule suspension, water-soluble concentrates, water-soluble powders, water-soluble granules, water-dispersible powders, water-dispersible granules, in the form of microgranules, microcapsules and waxes. These formulations are well-known in the art and are e.g. described, for example, by van Valkenburg, "Pesticide Formulations", Marcel Dekker N.Y 1973 ISBN: 9780824716950 0824716957 which is herewith incorporated by reference with respect to its entire disclosure content.

The C4 plant selective herbicide according to the invention is preferably identified using a method, comprising screening a compound library for a compound, which is
  i) capable of binding to the malate binding site comprised by a phosphoenolpyruvate carboxylase from a C4 plant (in particular, the allosteric feedback inhibitor binding site of PEPC from a C4 plant), thereby inhibiting the activity of said phosphoenolpyruvate carboxylase, and
  ii) not capable of binding to the malate binding site comprised by a phosphoenolpyruvate carboxylase from a C3 plant (in particular, to the allosteric feedback inhibitor binding site of PEPC from a C3 plant).

The term "herbicide" is well understood in the art. As used herein, the term refers to a compound that inhibits the growth of plants. The inhibition of the growth of plants shall include all deviations from natural development. In particular, the term refers to reducing the growth of the plant or to kill a plant. Moreover, the term may include inhibition of the development. Preferably, the term further includes dwarfing.

The herbicide according to the present invention shall be a C4 plant selective herbicide. A C4 plant selective herbicide, preferably, shall inhibit the growth of a C4 plant, but shall not inhibit the growth of a C3 plant. Also preferably, a C4 plant selective herbicide shall significantly inhibit the growth of a C4 plant, whereas growth of C3 plant shall remain unchanged, in particular essentially unchanged, in the presence of said herbicide (as compared to the absence of the herbicide). Whether growth of a plant is essentially unchanged or significantly inhibited can be determined by the skilled person without further ado.

Preferably, the compound is capable of binding to the malate binding site comprised by the phosphoenolpyruvate carboxylase from a C4 plant, but is not capable of binding to the malate binding site comprised by the phosphoenolpyruvate carboxylase from a C3 plant or binds only with significant lower affinity to the malate binding site comprised by the phosphoenolpyruvate carboxylase from a C3 plant.

The malate binding site of phosphoenolpyruvate carboxylase is well known in the art. In particular, is well known in the art that the regulation of the PEP carboxylase is, inter alia, effected by allosteric effectors, L-aspartate and L-malate. L-aspartate or L-malate which bind at the enzyme to an allosteric binding domain, the malate binding site (also called "aspartate binding site" or "aspartate/malate binding site", or "allosteric feedback inhibitor binding site", or "allosteric malate feedback inhibitor site"), thereby inhibiting the activity of the PEP carboxylase (see elsewhere herein). Accordingly, the malate binding site is, preferably, the allosteric feedback inhibitor binding site. The allosteric feedback inhibitor binding site from a C3 plant PEPC and from a C4 plant PEPC are, e.g., described and defined in Paulus et al., (2013a and 2013b) and by crystal structures 3ZGB and 3ZGE cited in these references. Both documents are herewith incorporated by reference with respect to their entire disclosure content.

Accordingly, the compound according to the use of the present invention, preferably, shall be capable of binding to the allosteric feedback inhibitor binding site of a PEPC from a C4 plant, but shall be not capable of binding to the allosteric feedback inhibitor binding site of a PEPC from a C3 plant or shall bind only with significant lower affinity to the allosteric feedback inhibitor binding site comprised by the phosphoenolpyruvate carboxylase from a C3 plant.

Figure 7:
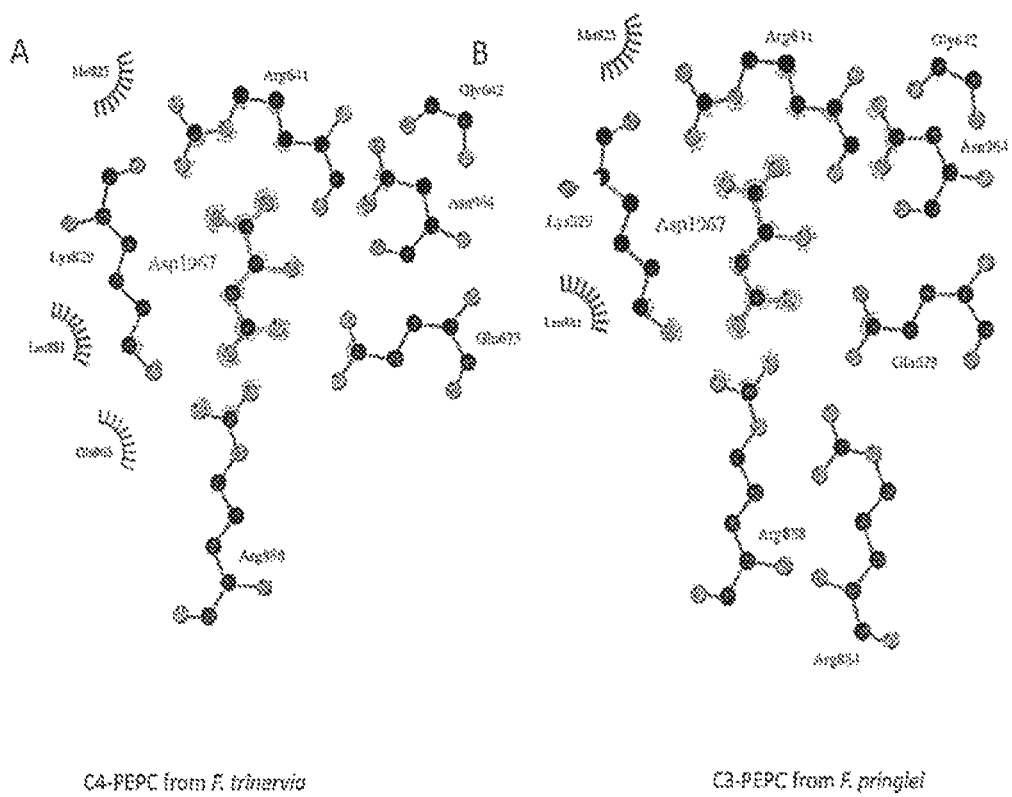
Figure 8:
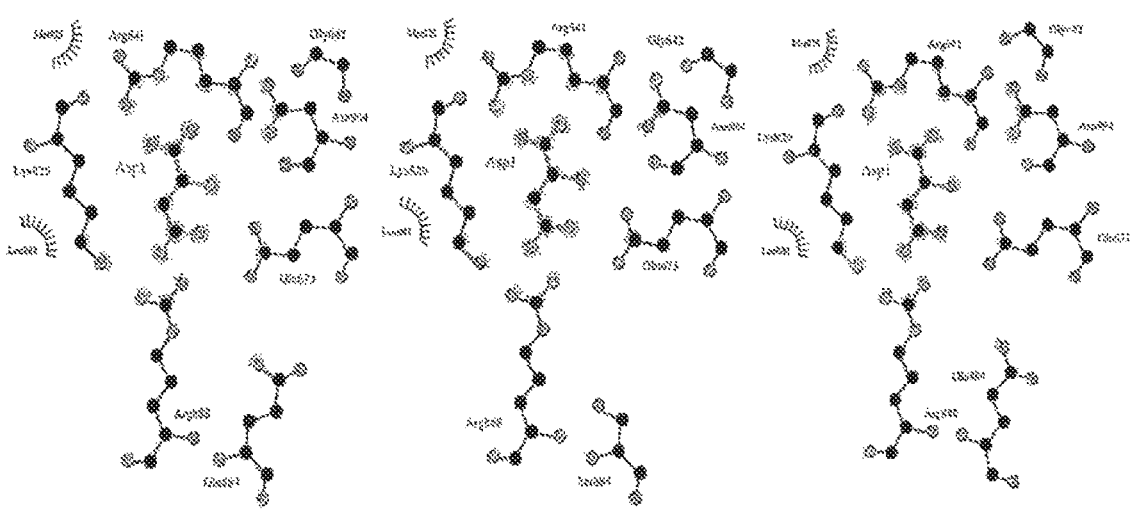

Thus, is also envisaged that the compound, preferably, shall be capable of binding to the malate binding site of a PEPC from a C4 plant as depicted in FIG. 7 A or FIG. 8, but shall be not capable of binding to the malate binding site of a PEPC from a C3 plant as depicted in FIG. 7 B (or shall bind only with significant lower affinity to the malate binding site of a PEPC from a C3 plant as depicted in FIG. 7 B).

As set forth above, the term "inhibiting the growth" also includes a "reducing the growth". Accordingly, it is envisaged that the growth of a C4 plant shall be reduced in the presence of said herbicide (in particular in the presence of an effective amount) as compared to the growth in the absence of said herbicide. In contrast, the growth of a C3 plant shall not be affected by the presence of the herbicide, in particular, shall not be significantly affected in the presence of said herbicide. Accordingly, a C3 plant, preferably, shows the same growth (in particular, essentially the same growth), regardless whether the herbicide is present or not. Thus, it is envisaged, that a C4 plant selective herbicide shall reduce the growth of a C4 plant, but shall not reduce the growth of a C3 plants.

It is to be understood that the inhibition of the growth of the C4 plant may dependent on the concentration. Preferably, the growth of the C4 plant is inhibited if the plant is contacted with an effective amount of the herbicide, i.e. with a herbicidal effective amount. Whether an amount of the herbicide is effective, or not, can be determined by methods known in the art.

The terms "C3 plant" and "C4 plant" are well understood by the skilled person.

A C3 plant, in particular, shall be a plant in which the $CO_2$ is first fixed into a compound containing three carbon atoms (phosphoglyceric acid) before entering the Calvin cycle of photosynthesis. Preferably, it uses the C3 carbon fixation pathway as the sole mechanism to covert $CO_2$ into 3-phosphoglycerate. C3 plants are well known in the art and include tobacco, tomato, soybeans, potato, cucumber, cotton, wheat, rice and barley.

Particularly preferred C3 plants are *Oryza sativa, Hordeum vulgare, Brassica napus, Triticum aestivum*, and, in particular, *Flaveria pringlei*. Further preferred are *Glycine max* (soybean), cucumber, grapes, potato, tomato, cassava, sugar beet and watermelon. Moreover, it is also preferred that the C3 plant is selected from the group of C3 plants consisting of asparagus, green beans, cabbages and other brassicas, carrots and turnips, cauliflowers and broccoli, green chilies and peppers, gherkins, eggplants, lettuce and chicory, pumpkins, squash and gourds, spinach, sunflower seed, and yams.

A C4 is plant in which the $CO_2$ is first fixed into a compound containing four carbon atoms before entering the Calvin cycle of photosynthesis. In particular, a C4 plant shall utilize the C4 carbon fixation pathway in which the $CO_2$ is first bound to a phosphoenolpyruvate resulting in the formation of four-carbon compound (oxaloacetate). C4 plants are well known in the art and include monocotyledonous plants such as maize, sugarcane, and sorghum, as well as dicotyledonous plants such as *Amaranthus*.

Preferably, the C4 plants belong to the C4 plants of the family selected from Aizoaceae (Genus, in particular, Cypselea, Gisekia, Trianthema, Zalaeya), Amaranthaceae (Acanthochiton, Aerva, Alteranthera, Amaranthus, Brayulinea), Caryophyllaceae (Polycarpaea), Chenopodiacea (Anabis, Aellenia, Arthrophytum, Atriplex, Bassia, Bienerta, Camphorosma, Chenolea, Climacoptera, Comulaca, Cytobasis, Echinopsilon, Gamanthus, Girgensohnia, Halanthium, Halimocnemis, Halocharis, Halogeton, Halostigmaria, Haloxylon, Hammada, Horaninovia, Hypocyclix, Kochia, Londesia, Noaea, Panderia, Petrosimonia, Salsola, Seidlitzia, Suaeda, Theleophyton, Traganum) Molluginaceae (Glinis, Mollugo) Nyctaginaceae (Ilionia, Boerhaavia, Okenia), Portulaceae (Portulaca), Polygonaceae (Calligonum), Euphorbiaceae (Chamaesyce, Euphorbia) Capparaceae (Gynandropsis), Zygophyllaceae (Kallstroemia, Tribulus, Zygophyllum) Asteraceae (Glossocordia, Glossogyne, Isostigma, Pectis), Boraginaceae, Convolvulaceae, Acanthaceae, Scrophulariaceae, Poaceae (Alloteropsis, Andropogon, Arundinella, Bouteloua, Cynodon, Echinochloa, Leptochloa, Microstegium, Panicum, Paspalum, Setaria, Sorghum, Spartina, Sporobolus, Zea). Preferred genera are indicated in brackets.

Particularly preferred C4 plants are selected from the group consisting of *Bothriochloa saccharoides, Bothriochloa ischaemum, Imperata cylindrica* (Cogon grass), *Panicum capillare* (Witchgrass), *Panicum coloratum, Panicum fluviicola, Panicum miliaceum, Panicum phragmitoides, Panicum turgidum, Saccharum officinarum* (Wild sugarcane), *Sorghum bicolor, Zea mays* (Maize), in particular *Flaveria trinervia, Setaria italica* (Foxtail millet), *Setaria palmifolia, Setaria plicata, Paspalum conjugatum* (Buffalo Gras), *Paspalum quadrifarium, Paspalum dilatatum, Amaranthus hypochondriacus, Amaranthus spinosus* (spiny amaranth), *Sorghum halepense* (Johnsongrass), *Rottboellia cochinchinensis* (itchgrass), *Commelina benghalensis* (tropical spiderwort), *Trianthema portulacastrum* (desert horse purslane), *Ageratum conyzoides* (Chick weed, Goatweed, Whiteweed), *Bidens pilosa* (Spanish Needle), *Euphorbia hirta, Portulaca oleracea* (Pigweed). Further preferred C4 plants are *Alopecurues myosuroides* and *Gallium aparine*. Particularly preferred C4 plants are *Flaveria trinervia, Flaveria australasica, Zea mays*, and *Sorghum bicolor*.

The phosphoenolpyruvate carboxylases to be used in the context of the present invention shall be derived from a C3 and from a C4 plant, respectively. Thus, it is particular envisaged that the phosphoenolpyruvate carboxylase to be used is naturally present in a C3 and a C4 plant, respectively. It is also contemplated that the phosphoenolpyruvate carboxylase may be a recombinant and/or mutated phosphoenolpyruvate carboxylase present in plant as transgene. Preferred C3 and C4 plants are disclosed herein above.

The term "phosphoenolpyruvate carboxylase" is well understood by the skilled person. Frequently, phosphoenolpyruvate carboxylases are also referred to as PEP carboxylase, PEPCase, or PEPC. A phosphoenolpyruvate carboxylase as referred to herein shall be capable of catalyzing the formation of oxaloacetate from phosphoenolpyruvate (PEP) and bicarbonate (EC 4.1.1.31). In particular, a phosphoenolpyruvate carboxylase shall be capable of catalyzing the irreversible beta-carboxylation of phosphoenolpyruvate by bicarbonate to yield oxalacetate and phosphate. The aforementioned enzymatic activity can be determined by assays well known in the art.

It is well known in the art, that the regulation of the PEP carboxylase is, inter alia, effected by allosteric effectors, L-aspartate and L-malate. L-aspartate or L-malate bind at the enzyme to an allosteric binding domain, the malate binding site (also called "aspartate binding site" or "aspartate/malate binding site", or "allosteric feedback inhibitor binding site", or "allosteric malate feedback inhibitor site"), thereby inhibiting the activity of the PEP carboxylase. The malate binding site of a PEP carboxylase comprises four conserved residues which participate directly in the binding of malate and aspartate. The conserved residues are well known in the art, and e.g. described by Jacobs et al. (Plant Cell and Environment (2008), 31, 793-803). In *Flaveria*, the four conserved residue which participate in the binding of aspartate/malate are R641, K829, R888 and N964 (see the sequences disclosed herein for the PEPC from *Flaveria pringlei* and *Flaveria trinervia*).

In a preferred embodiment of the present invention the PEP carboxylase from a C4 plant is derived from *Flaveria trinervia* (GenBank Accession Number CAA43601.1 GI:498699), and the PEP carboxylase from a C3 plant is derived from *Flaveria pringlei* (GenBank Accession number CAA45505.1 GI:18458), i.e. two highly homologous PEP carboxylases. The amino acid sequence of the PEP carboxylase from *Flaveria trinervia* is shown in SEQ ID NO: 1, the amino acid sequence of the PEP carboxylase from *Flaveria pringlei* is shown in SEQ ID NO: 2.

Thus, in a preferred embodiment, the phosphoenolpyruvate carboxylase derived from a C4 plant is, in particular, encoded by a polynucleotide comprising a nucleic acid selected from the group consisting of:
 a. a nucleic acid encoding a polypeptide having an amino acid sequence as shown in SEQ ID No: 1;
 b. a nucleic acid encoding a polypeptide having an amino acid sequence being at least 90%, 95%, 97% or in particular 99% identical to the amino acid sequence shown in SEQ ID No: 1, wherein said polypeptide has phosphoenolpyruvate carboxylase activity.

The enzymatic activity of a PEP carboxylase is disclosed elsewhere herein. Thus, the phosphoenolpyruvate carboxylase shall be capable of catalyzing the formation of oxaloacetate from phosphoenolpyruvate (PEP) and bicarbonate (EC 4.1.1.31, see above). Preferably, the phosphoenolpyruvate carboxylase derived from a C4, comprises, within its malate binding site, a glycine residue which corresponds to the conserved glycine residue found at position 884 of the PEP carboxylase from *Flaveria pringlei*. Moreover, the inventors have found that some of the PEP carboxylases from C4 plants comprise at a position which corresponds to the glycine residue, a serine, glutamine or isoleucine residue, i.e. amino acid residues which will also not inhibit binding of the identified herbicides by their side-chain. Alternatively, the said phosphoenolpyruvate carboxylase derived from a C4, comprises, within its malate binding site, a serine, glutamine or isoleucine residue which corresponds to said glycine residue. The malate binding site of the PEP Carboxylase from *Flaveria trinervia* is well known in the art, and, e.g. described by Jacobs et al. (Plant Cell and Environment (2008), 31, 793-803). Preferably, the variants of the phosphoenolpyruvate carboxylase set forth in b. above are capable of binding malate.

Thus, in a preferred embodiment, the phosphoenolpyruvate carboxylase derived from a C3 plant is, in particular, encoded by a polynucleotide comprising a nucleic acid selected from the group consisting of:
 a. a nucleic acid encoding a polypeptide having an amino acid sequence as shown in SEQ ID No: 2;
 b. a nucleic acid encoding a polypeptide having an amino acid sequence being at least 90%, 95%, 97% or in particular 99% identical to the amino acid sequence shown in SEQ ID No: 2, wherein said polypeptide has phosphoenolpyruvate carboxylase activity.

The activity of a PEP carboxylase is disclosed elsewhere herein. Preferably, the phosphoenolpyruvate carboxylase derived from a C3, comprises, within its malate binding site, a conserved arginine residue which corresponds to the conserved arginine residue found at position 884 of the PEP carboxylase from *Flaveria pringlei*. Preferably, the conserved arginine residue is within the region of amino acid 875 to 895. The malate binding site of the PEP Carboxylase from *Flaveria pringlei* is well known in the art, and, e.g. described by Jacobs et al. (Plant Cell and Environment (2008), 31, 793-803), which is herewith incorporated by reference with respect to its entire disclosure content. Preferably, the variants of the phosphoenolpyruvate carboxylase set forth in b. above are capable of binding malate.

The term "polynucleotide" as used herein refers to a linear or circular nucleic acid molecule. It encompasses DNA as well as RNA molecules. The polynucleotide of the present invention shall be provided, preferably, either as an isolated polynucleotide (i.e. isolated from its natural context) or in genetically modified form. The term encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides. The polynucleotide of the present invention is characterized in that it shall encode a polypeptide as referred to above. The polynucleotide, preferably, has a specific nucleotide sequence as mentioned above. Moreover, due to the degeneracy of the genetic code, polynucleotides are encompassed which encode a specific amino acid sequence as recited above.

Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the polynucleotide or the amino acid sequence of the polypeptide of the present invention with sequences of other members of the enzyme families referred to in accordance with this invention. Oligonucleotides suitable as PCR primers as well as suitable PCR conditions are described in the accompanying Examples. As a template, DNA or cDNA from bacteria, fungi, plants or Animals may be used. Further, variants include polynucleotides comprising nucleic acid sequences which are, in increasing order of preference, at least 70%, at least 75%, at least 80%, at least 85%, at least 90%, at least 95%, at least 98% or at least 99% identical to the specific nucleic acid sequences. Moreover, also encompassed are polynucleotides which comprise nucleic acid sequences encoding amino acid sequences which are, in increasing order of preference, at least 70%, at least 75%, at least 80%, at least 85%, at least 90%, at least 95%, at least 98% or at least 99% identical to the specific amino acid sequences referred to herein. The percent identity values as set forth herein are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program Pileup (Higgins 1989, CABIOS, 5 1989: 151-153) or the programs Gap and BestFit (Needleman 1970, J. Mol. Biol. 48; 443-453 and Smith 198, Adv. Appl. Math. 2; 482-489), which are part of the GCG software packet from Genetics Computer Group, 575 Science Drive, Madison, Wis., USA 53711, version 1991, are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the aforementioned nucleic acid sequences is also encompassed as a polynucleotide of the present invention. The fragment shall encode a polypeptide which still has the activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part peptide sequences for monitoring expression or protein-protein interaction (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

Further preferred PEP carboxylases from C3 plants are derived from the following plants (indicated is the organism, the GenBank Accession Nummer, and the position of the conserved arginine residue. For some enzymes, only the sequences of fragments are known, the full length sequences can be determined by the skilled person without further ado):

| | |
|---|---|
| *Oryza sativa* (Rice) EMBL AAG00180.1 | R879 |
| *Brassica napus* (Rape) TrEMBL Q42634 | R883 |
| *Triticum aestivum* (Wheat) EMBL CAA07610.1 | R891 |
| *Phaseolus vulgaris* (Kidney bean) UniProtKB/Swiss-Prot Q9AU12 | R887 |
| *Hordeum vulgare* (Barley) EMBL ABB01326.1 (Fragment) | R146 |
| *Vicia faba* (Broad bean) (*Faba vulgaris*) EMBL CAA09588.1 | R885 |
| *Cucumis sativus* (Cucumber) EMBL CAD10147.1 (Fragment) | R117 |
| *Vitis vinifera* (Grape) EMBL AAL83719.1 (Fragment) | R258 |
| *Solanum tuberosum* (Potato) UniProtKB/Swiss-Prot P29196 | R885 |
| *Gossypium hirsutum* (Upland cotton) EMBL AAB80714.1 | R884 |
| *Glycine max* (Soybean) UniParc P51061 | R886 |
| *Nicotiana tabacum* (Common tobacco) UniParc P27154 | R884 |

Further preferred PEP carboxylases from C3 plants are derived from *Hordeum vulgare* (BAJ88050.1 GI:326516054) or from *Arabidopsis thaliana* (AAC24594.1 GI:3264805)

Further preferred PEP carboxylases from C4 plants are derived from the following plants (indicated is the organism, the GenBank Accession Nummer, and the position of the conserved glycine residue, alternatively of the serine, glutamine or isoleucine, see elsewhere herein. For some enzymes, only the sequences of fragments are known, the full length sequences can be determined by the skilled person without further ado):

| | |
|---|---|
| *Bothriochloa saccharoides* (Fragment) TrEMBL A7DX44 | G429 |
| *Bothriochloa ischaemum* (Fragment) TrEMBL A7DX82 | G429 |
| *Imperata cylindrica* (Cogon grass) Fragment) TrEMBL A7DX63 | G429 |
| *Panicum capillare* (Witchgrass) (Fragment) EMBL CAM84110.1 | G429 |
| *Panicum coloratum* (Fragment) TrEMBL A7DXB1 | G429 |
| *Panicum fluviicola* (Fragment) TrEMBL D9UAH3 | G721 |
| *Panicum miliaceum* (Fragment) TrEMBL E1XUD1 | G721 |
| *Panicum phragmitoides* (Fragment) TrEMBL D9UAH8 | G721 |
| *Panicum turgidum* (Fragment) TrEMBL D9UAH5 | G721 |
| *Saccharum spontaneum* (Wild sugarcane) EMBL CAC85930.1 | G881 |
| *Saccharum officinarum* (Wild sugarcane) EMBL CAC08829.1 | G881 |
| *Sorghum bicolor* Swiss-prot P15804 | G881 |
| *Zea mays* (Maize) EMBL CAA33317.1 | G890 |
| *Flaveria trinervia* Swiss-Prot P30694 | G884 |
| *Flaveria australasica* NCBI GenBank Z25853.1 | G884 |
| *Panicum laetum* (Fragment) EMBL CAM84117.1 | S429 |
| *Setaria italica* (Foxtail millet) TrEMBL Q8S2Z8 | Q884 |
| *Setaria palmifolia* (Fragment) TrEMBL A7DXC5 | Q429 |
| *Setaria plicata* (Fragment) TrEMBL A7DXC6 | Q429 |
| *Paspalum conjugatum* (Buffalo Gras) (Fragment) TrEMBL A7DXB6 | Q429 |

| | |
|---|---|
| *Paspalum quadrifarium* (Fragment) EMBL CAM84120.1 | Q429 |
| *Paspalum dilatatum* (Fragment) TrEMBL A7DXB7 | Q429 |
| *Amaranthus hypochondriacus* SwissProt Q43299 | I884 |

How to determine the activity of a PEP carboxylase is well known in the art. E.g., the formation of oxaloacetate can be determined spectrophotometrically, e.g., in a malate dehydrogenase coupled system. The reaction velocity can be measured as a decrease in $A_{340}$ resulting from the oxidation of NADH.

Preferably, a compound which inhibits the growth of a C4 plant, but which does not inhibit the growth of the C3 plant can be used as C4 selective herbicide.

By way of example, the following particularly preferred embodiments of the invention are described:

1. Use of at least one compound, or salt or solvate thereof, as C4 plant selective herbicide wherein said compound has a structure according to
   (a) formula (I)

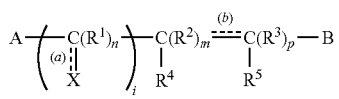

(I)

wherein A is a cyclic alkyl, aryl, heterocycloalkyl, or heteroaryl group, and B is a cyclic alkyl, aryl, heterocycloalkyl, or heteroaryl group, wherein A is a cyclic alkyl, aryl, heterocycloalkyl, or heteroaryl group, and B is a cyclic alkyl, aryl, heterocycloalkyl, or heteroaryl group, and wherein $R^1$, $R^2$, $R^3$, $R^4$ and $R^5$ are, independently of each other H or an alkyl group, and wherein integer i is 0 or 1, preferably 1 and wherein the bond (a) is a single or double bond, and wherein in case (a) is a double bond, n is 0 and X is O or S, and wherein in case (a) is a single bond n is 1, and X is H or an alkyl group, and wherein the bond (b) is a single or double bond, and wherein in case (b) is a double bond, m and p are 0, and wherein in case (b) is a single bond m and p are both 1, and/or (b) formula (II)

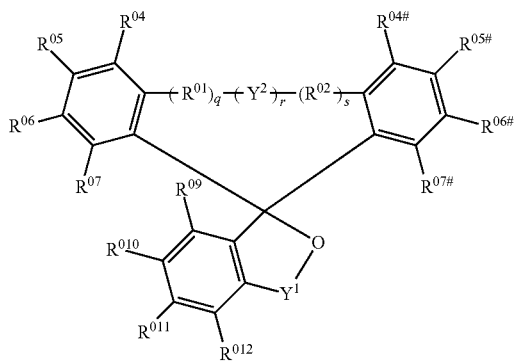

(II)

wherein $R^{01}$ and $R^{02}$ are independently of each other selected from the group consisting of H, OH, carboxylic acid, ester, alkyl, alkoxy and halogen, wherein $Y^1$ is selected from the group consisting of (S(=O)2), S(=O)) and (C(=O))

and wherein $Y^2$ is O, and wherein r is 0 or 1 and wherein in case r is 0, q and s are 1, and wherein in case r is 1, q and s are 0, and wherein $R^{01}$, $R^{02}$, $R^{04}$, $R^{05}$, $R^{06}R^{07}$, $R^{04\#}$, $R^{05\#}$, $R^{06\#}$, $R^{07\#}$, $R^{09}$, $R^{010}$, $R^{011}$ and $R^{012}$, are independently of each other selected from the group consisting of H, OH, —SO$_3$H, carboxylic acid, ester, alkyl, alkoxy and halogen, said compound being capable of binding to the malate binding site comprised by a phosphoenolpyruvate carboxylase from a C4 plant, thereby inhibiting said phosphoenolpyruvate carboxylase.

2. Use according to embodiment 1, wherein the binding to the malate binding site of a phosphoenolpyruvate carboxylase from a C3 plant is inhibited, preferably by steric or electrostatic constraints of a conserved arginine in the binding site of the C3 PEPC, preferably by Arg-884 in *Flaveria pringlei*.

3. Use according to embodiment 1 or 2, wherein compound has a structure according to formula (I) and wherein A is

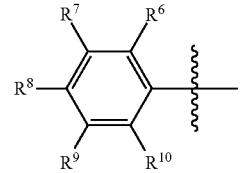

wherein $R^6$, $R^7$, $R^8$, $R^9$ and $R^{10}$ are, independently of each other, selected from the group consisting of H, OH, carboxylic acid, ester, alkyl, alkoxy and halogen, or wherein two residues in ortho position to each other form a cyclic or heterocyclic ring, preferably wherein at least one of $R^6$, $R^7$, $R^8$, $R^9$ and $R^{10}$ is OH.

4. Use according to any one of embodiments 1 to 3, wherein compound has a structure according to formula (I) and wherein B is

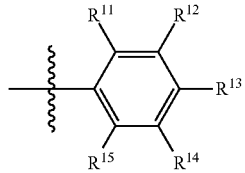

wherein $R^{11}$, $R^{12}$, $R^{13}$, $R^{14}$ and $R^{15}$ are, independently of each other, selected from the group consisting of H, OH, carboxylic acid, ester, alkyl, alkoxy and halogen, or wherein two residues in ortho position to each other form a cyclic or heterocyclic ring.

5. Use according to any one of embodiments 1 to 3, wherein compound has a structure according to formula (I) and wherein n is 0, (a) is a double bond and X is O or S, preferably O, more preferably wherein the compound has the structure

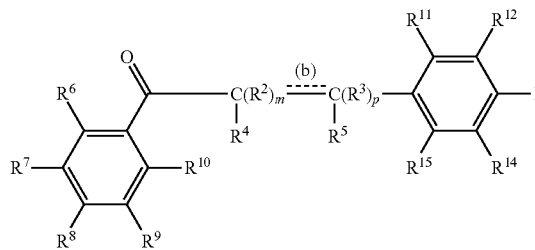

wherein $R^6$, $R^7$, $R^8$, $R^9$, $R^{10}$ $R^{11}$, $R^{12}$, $R^{13}$, $R^{14}$ and $R^{15}$ are, independently of each other, selected from the group consisting of H, OH, carboxylic acid, ester, alkyl, alkoxy and halogen, more preferably wherein at least one of $R^6$, $R^7$, $R^8$, $R^9$ and $R^{10}$ is OH.

6. Use according to embodiment 5, wherein b is a double bond and the compound has the structure

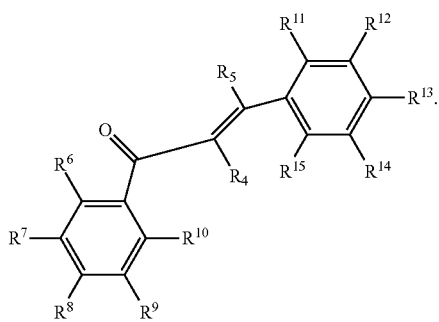

7. Use according to embodiment 5, wherein b is a single bond and the compound has the structure

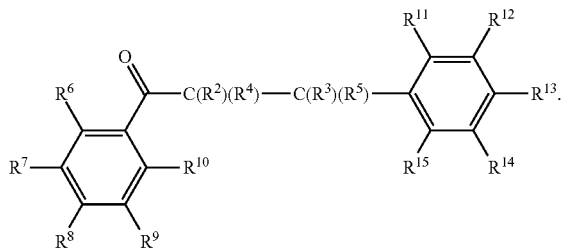

8. Use according to any one of embodiments 1 to 3, wherein n is 1, (a) is a single bond and X is H or alkyl, more preferably wherein the compound has the structure

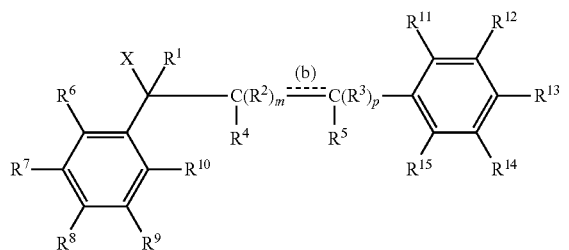

9. Use according to embodiment 8, wherein b is a double bond and the compound has the structure

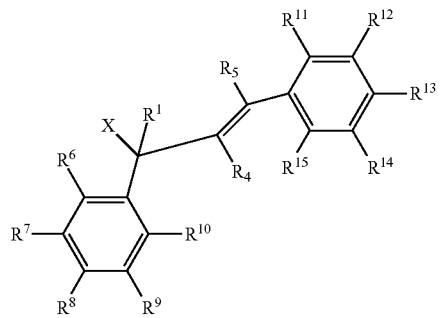

10. Use according to embodiment 5, wherein b is a single bond and the compound has the structure

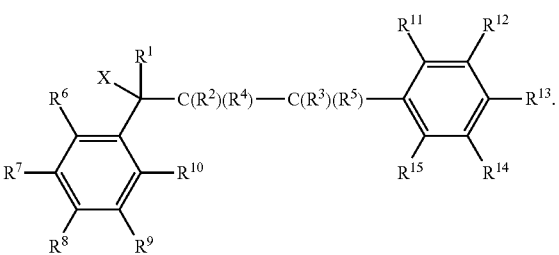

11. Use according to embodiment 1 or 2, wherein in formula (II) $Y^2$ is O, and wherein r is 1 and wherein q and s are 0, the compound having the structure

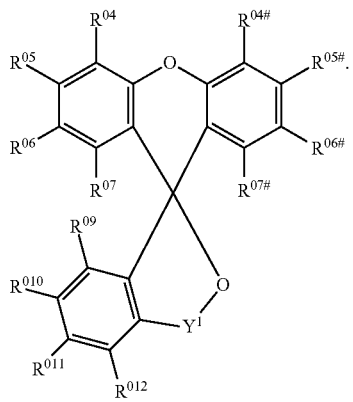

12. Use according to embodiment 1 or 2, wherein in formula (II) wherein r is 0 and wherein q and s are 1, the compound having the structure

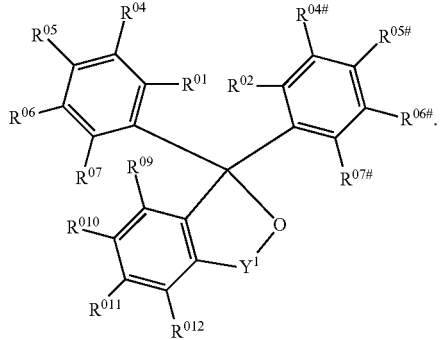

13. Use according to embodiment 11 or 12, wherein $R^{04}$, $R^{07}$, $R^{04\#}$, $R^{07\#}$, $R^{09}$, and $R^{012}$ are H.
14. Use according to any one of embodiments 11 to 13, wherein $Y^1$ is (S(=O)2).
15. Use according to any one of c embodiments 11 to 13, wherein $Y^1$ is (S(=O)).
16. Use according to any one of embodiments 11 to 13, wherein $Y^1$ is (C(=O)).
17. Use according to any one of embodiments 11 to 116, wherein $R^{05}$, $R^{06}$, $R^{05\#}$, $R^{06\#}$ are OH.

The figures show:

FIG. 1: Partial alignment of PEP carboxlyases derived from various C3 and C4 plants. Indicated are the conserved arginine residues in C3 PEP carboxylases, and the conserved glycine residues in C4 PEP carboxylases. Numbering is according to *Flaveria pringlei* and *Flaveria trinervia*.

FIG. 2: Selective inhibition of a C4-PEPC by butein. Activity of C4 PEPC was measured over a range of butein concentrations. The half maximal (50%) inhibitory concentration (IC50) of butein for C4 PEPC was determined from these data that were measured in triplicate for each concentration. Corresponding activity of a C3 PEPC at the IC50 concentration of butein for the C4 enzyme is also indicated in the Figure.

Figure 3:
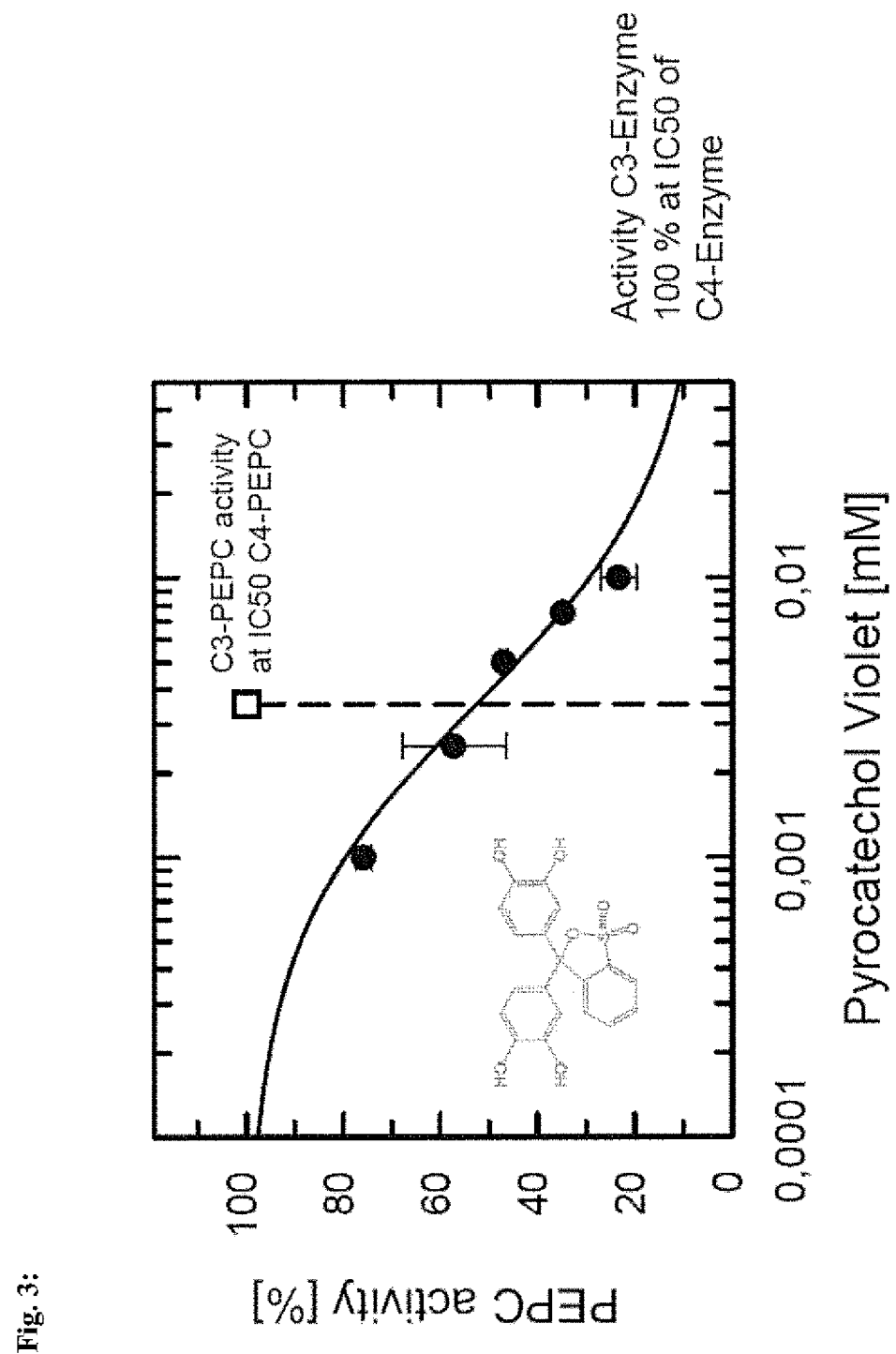

FIG. 3: Selective inhibition of a C4-PEPC by pyrocatechol violet. Activity of C4 PEPC was measured over a range of pyrocatechol violet concentrations. The half maximal (50%) inhibitory concentration (IC50) of pyrocatechol violet for C4 PEPC was determined from these data that were measured in triplicate for each concentration. Corresponding activity of a C3 PEPC at the IC50 concentration of pyrocatechol violet for the C4 enzyme is also indicated in the Figure.

Figure 4:
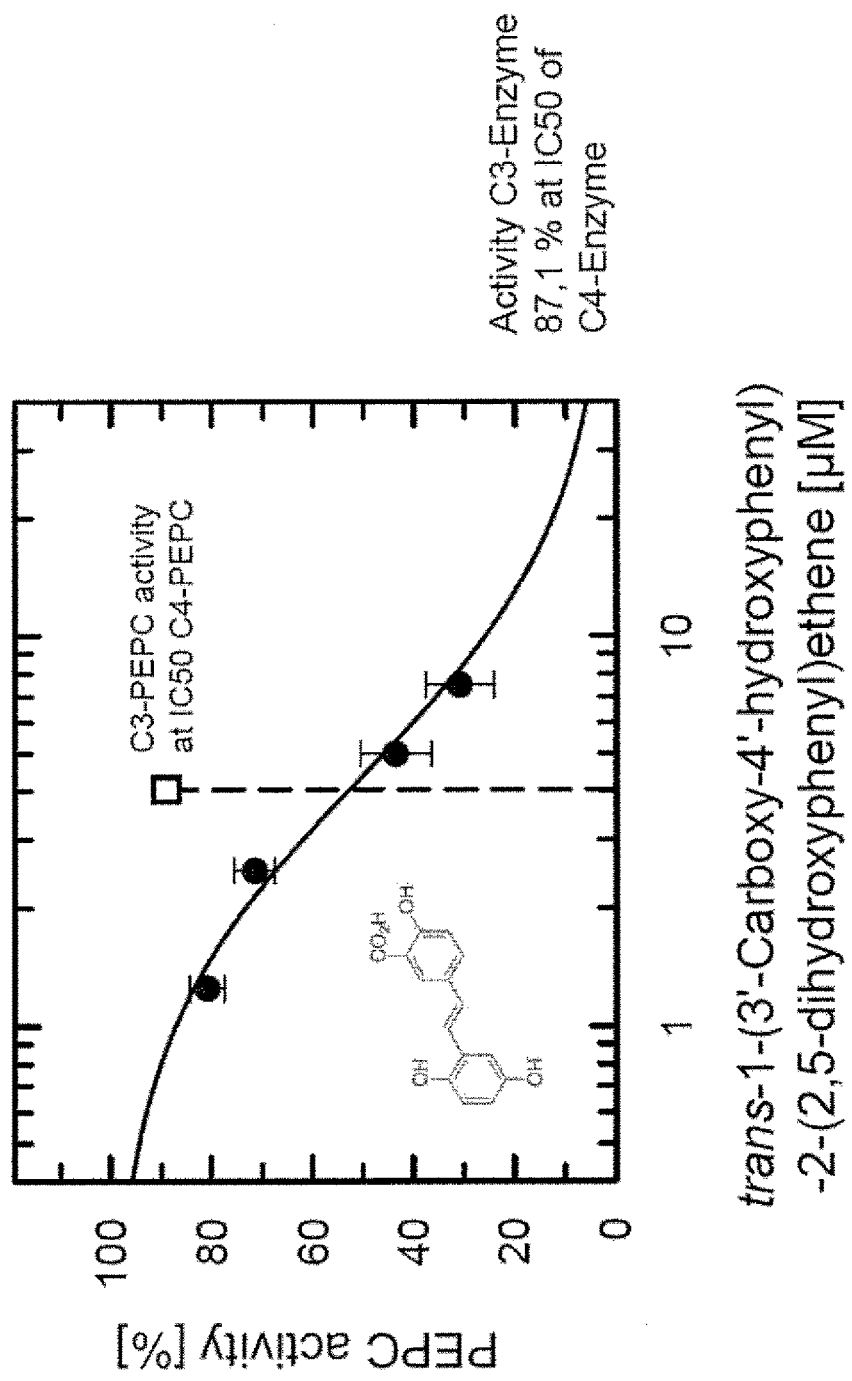

FIG. 4: Selective inhibition of a C4-PEPC by 1-(3'-carboxy-4'-hydroxyphenyl)-2-(2,5-dihydroxyphenl(ethene). Activity of C4 PEPC was measured over a range of 1-(3'-carboxy-4'-hydroxyphenyl)-2-(2,5-dihydroxyphenl(ethene) concentrations. The half maximal (50%) inhibitory concentration (IC50) of 1-(3'-carboxy-4'-hydroxyphenyl)-2-(2,5-dihydroxyphenl(ethene) for C4 PEPC was determined from these data that were measured in triplicate for each concentration. Corresponding activity of a C3 PEPC at the IC50 concentration of 1-(3'-carboxy-4'-hydroxyphenyl)-2-(2,5-dihydroxyphenl(ethene) for the C4 enzyme is also indicated in the Figure.

Figure 5:
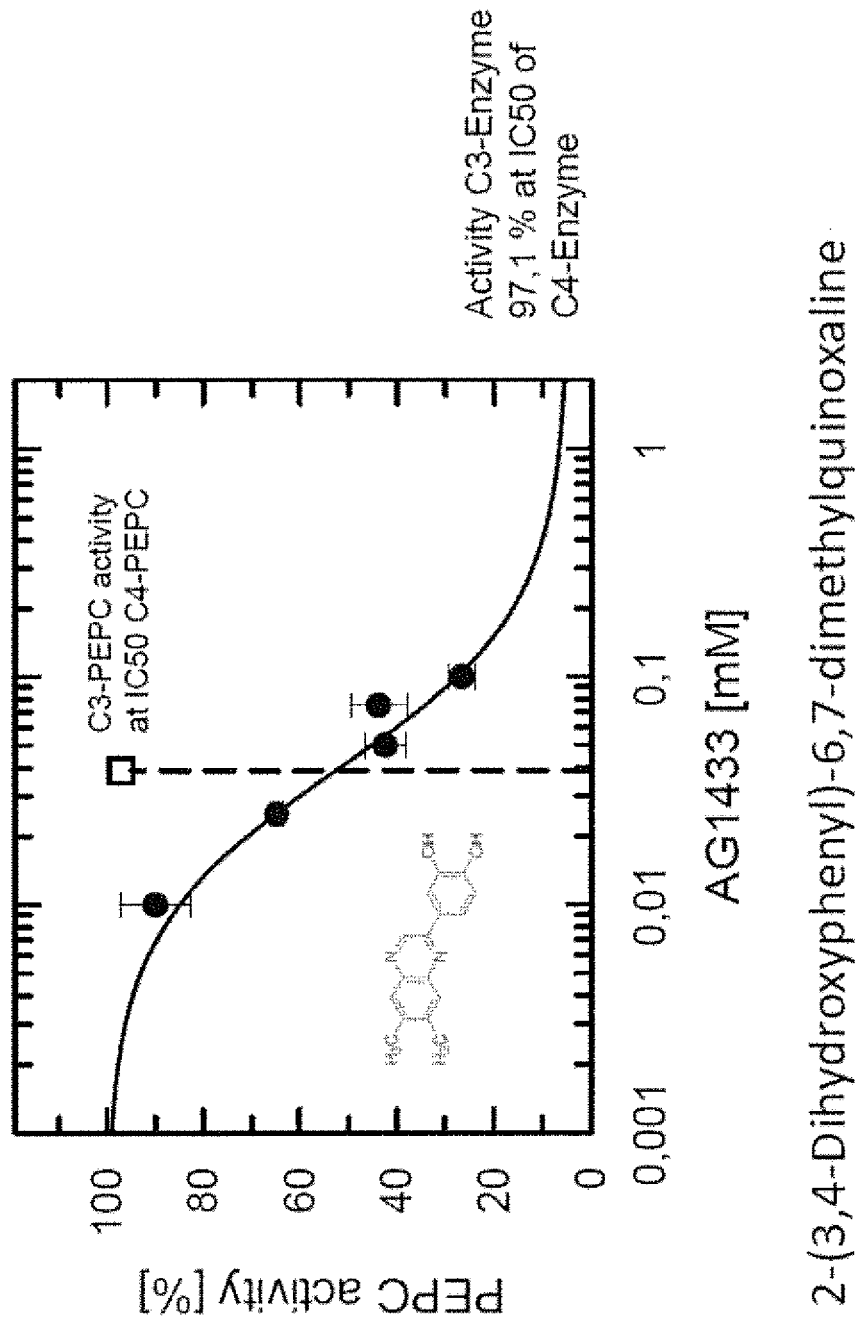

FIG. 5: Inhibition of a C4-PEPC by 2-(3,4-Dihydroxyphenyl)-6,7-dimethoxyquinoxaline (compound not according to the invention). Activity of C4 PEPC was measured over a range of 2-(3,4-Dihydroxyphenyl)-6,7-dimethoxyquinoxaline concentrations. The half maximal (50%) inhibitory concentration (IC50) of 2-(3,4-Dihydroxyphenyl)-6,7-dimethoxyquinoxaline for C4 PEPC was determined from these data that were measured in triplicate for each concentration. Corresponding activity of a C3 PEPC at the IC50 concentration of 2-(3,4-Dihydroxyphenyl)-6,7-dimethoxyquinoxaline for the C4 enzyme is also indicated in the Figure.

Figure 6:
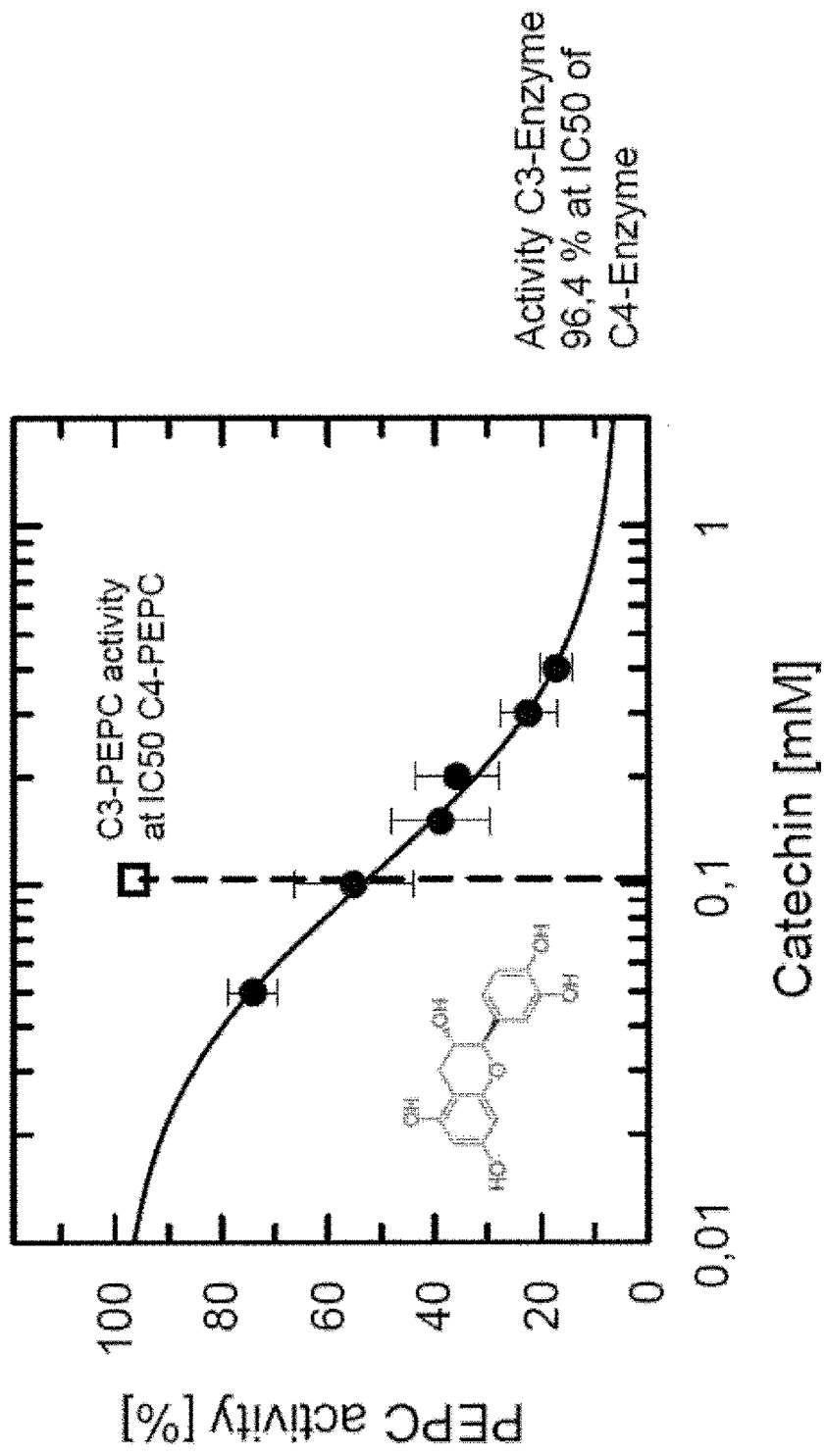

FIG. 6: Inhibition of a C4-PEPC by catechin (compound not according to the invention). Activity of C4 PEPC was measured over a range of catechin concentrations. The half maximal (50%) inhibitory concentration (IC50) of catechin for C4 PEPC was determined from these data that were measured in triplicate for each concentration. Corresponding activity of a C3 PEPC at the IC50 concentration of catechin for the C4 enzyme is also indicated in the Figure.

FIG. 7: Side by side comparison of the Allosteric Feedback Inhibitor Binding Site (Malate Binding Site) in PEPC. (A) Inhibitor-binding site of C4-PEPC (*F. trinervia*). (B) Inhibitor Binding Site of C3-PEPC (*F. pringlei*). Residues Arg641, Lys829, Arg888 and Asn964 have been identified as the malate-binding motif. In C3-PEPC, Arg884 provides an additional hydrogen bond for inhibitor binding. In C4-PEPC, this residue is replaced by glycine, which is 6.9 Å away from the inhibitor molecule. The bound feedback inhibitor is shown in the center of the binding site and labelled Asp1. Figures were made using LIGPLOT (Wallace et al., 1995).

FIG. 8: Allosteric Feedback Inhibitor Binding Site (Malate Binding Site) of C4-type PEPCs. Residues Arg641, Lys829, Arg888 and Asn964 (*Flaveria* numbering) have been identified as the malate-binding motif. In C3-PEPCs (see FIG. 7 B) Arg884 provides an additional hydrogen bond for inhibitor binding. In C4-PEPCs, this residue is replaced by glycine, glutamine, serine or glutamate (see Paulus et al., 2013a and 2013b). The bound feedback inhibitor is shown in the center of the binding site and labelled Asp1. Figures were made using LIGPLOT (Wallace et al., 1995).

The following Examples shall merely illustrate the invention. They shall not be construed, whatsoever, to limit the scope of the invention.

EXAMPLE 1

The histidine-tagged PEP carboxylase from *Flaveria pringlei* or from *Flaveria trinervia* was heterologously expressed in *E. coli* and purified via immobilized metal affinity chromatography (IMAC). Crystals of the C3 (*F. pringlei*) and the C4 (*F. trinervia*) PEP carboxylase were obtained from the purified proteins by microbatch vapor diffusion. Crystals where analyzed by synchrotron radiation and PEPC structures were determined from the diffraction data by molecular replacement using XDS, coot and the CCP4 suite (Kabsch, 2010; Emsley et al. 2004; CCP4, 1994).

Crystal structures of PEP carboxylase from *Flaveria pringlei* (PDB code: 3ZGB) or from *Flaveria trinervia* (PDB code: 3ZGE) were superimposed by the alignment algorithm of PyMOL (DeLano, 2002) which performs a BLAST-like BLOSUM62-weighted dynamic programming sequence alignment followed by a series of refinement cycles intended to improve the fit by eliminating pairing with high relative variability. The malate binding site in the aligned crystal structures was visually inspected for structural differences in the region of 10-15 Å around the bound aspartate inhibitor. From this alignment the structural difference in position 884 was identified. The C3 type PEP carboxylase of *Flaveria pringlei* has a voluminous arginine side chain in this position, while the C4 type PEP carboxylase of *Flaveria trinervia* carries a small glycine residue in the corresponding position.

Potential selective inhibitors of C4 PEP carboxylase were selected from a Virtual Drug Screening (VDS) approach using the program PyRX (Wolf, 2009), standard compound libraries (ChemBank, NCI DataBase, KEGG Database), a library assembled from the Plant Metabolome Database and the high resolution crystal structures of PEP carboxylases from *F. pringlei* and *F. trinervia*.

In particular, the potential selective inhibitors of C4 PEP carboxylase shown in Table 3 and Table 4 as well as in FIGS. 5 and 6 were identified:

EXAMPLE 2

Confirmation of Selective Inhibition of Selected Compounds

Inhibition of purified PEP carboxylases from *F. pringlei* and *F. trinervia* by compounds selected from the VDS was monitored by a spectrophotometric coupled assay with malate dehydrogenase which reduces the oxaloacetate formed by PEP carboxylase to malate. The simultaneous oxidation of NADH is followed at 340 nm with standard optical equipment. The concentration of the inhibitors selected from the VDS was varied in the coupled assay to determine the half maximal inhibitory concentration (IC50).

With butein and pyrocatchol violet, the inhibition shown in FIGS. 2 and 3 of the PEP carboxylase activity of the C3 and the C4 enzyme was obtained. With 1-(3'-carboxy-4'-hydroxyphenyl)-2-(2,5-dihydroxyphenl(ethene), the inhibition shown in FIG. 4 of the PEP carboxylase activity of the C3 and the C4 enzyme was obtained. Further results are given in Table 3 and Table 4. Comparative examples for compounds described earlier in PCT/EP2012/076648 are given in FIGS. 5 and 6.

EXAMPLE 3

Determination of the Binding Constant of C4-Selective Inhibitors in the Presence and in the Absence of the Natural Feedback Inhibitor Malate The dissociation constants (Kd) of PEPC from *F. trinervia* for putative C4-selective inhibitors (for details see Table below) will be determined by microscale thermophoresis (MST, Duhr and Braun, 2006; Jerabek-Willemsen et al., 2011) using the Monolith NT.115 (NanoTemper Technologies, Munich, Germany). Measurements will be done in the absence and in the presence of the natural feedback inhibitor malate (20 mM) in order to allow or to protect binding of the C4-selective inhibitor to the allosteric malate feedback inhibitor site.

Purified protein is buffered in 50 mM potassium phosphate (pH 7.6), 150 mM NaCl, 0.05% Tween 20 and labelled with NT-547-Maleimide (NanoTemper Technologies) according to the protocol of the manufacturer. The compounds are dissolved in organic solvents like DMSO, acetone or ethanol or in aqueous buffer solutions at high concentrations.

For MST measurements the stock solutions are diluted with protein buffer (50 mM potassium phosphate (pH 7.6), 150 mM NaCl, 0.05% Tween 20). The above solvent is used to prepare a 1:1 serial dilution in 16 dilution steps. 10 µl of the compound dilution is mixed with 10 µl protein solution and filled into capillaries. The compound concentration is highest in the first capillary and decreases in the next capillaries according to the 1:1 dilution. Data are fitted according to a cooperative binding model.

TABLE 1

Substances to be tested in binding studies by microscale thermophoresis

Butein
Robtein
Piceatannol
trans-1-(3'-Carboxy-4'-hydroxyphenyl)-2-(2,5-dihydroxyphenyl)ethene
Pyrocatechol Violet
Gallein
Cresol Red
Chrome Cyanine R

REFERENCES

Collaborative Computational Project, Number 4 (1994) The CCP4 Suite: Programs for Protein Crystallography. Acta Cryst. D50, 760-763.

DeLano, WL, (2002) The PyMOL Molecular Graphics System, DeLano Scientific, San Carlos, CA, USA.

Doyle, JR, Burnell, JN, Haines, DS, Llewellyn, LE, Motti, CA and Tapiolas, DM (2005) A Rapid Screening Method to Detect Specific Inhibitors of Pyruvate Orthophosphate Dikinase as Leads for C4 Plant-Selective Herbicides. J Biomol Screen 10: 67-75.

Duhr, S and Braun, D (2006). Why molecules move along a temperature gradient. Proc. Natl. Acad. Sci. USA 103, 19678-19682.

Durrant, JD, Amaro, RE and McCammon, JA (2009) Auto-Grow: A Novel Algorithm for Protein Inhibitor Design. Chemical Biology & Drug Design 73(2):168-178.

Emsley, P and Cowtan, K (2004) Coot: model-building tools for molecular graphics. Acta Crystallographica Section D-Biological Crystallography 60: 2126-2132 Part 12 Sp. Iss.

Jenkins, CLD, Harris, RLN and McFadden, HG (1987) 3,3-Dichloro-2-dihydroxyphosphinoylmethyl-2-propenoate, a new, specific inhibitor of phosphoenolpyruvate carboxylase. Biochem Int 14:219-226.

Jenkins, CLD (1989) Effects of the phosphoenolpyruvate carboxylase inhibitor 3,3-dichloro-2-(dihydroxyphosphinoylmethyl)propenoate on photosynthesis. Plant Physiol 89:1231-1237.

Jerabek-Willemsen, M, Wienken, CJ, Braun, D, Baaske, P and Duhr, S (2011). Molecular Interaction Studies Using Microscale Thetinophoresis. Assay Drug Dev. Technol. 9, 342-353.

Kabsch, W (2010) XDS. Acta Cryst. D66, 125-132.

Mancera, RL, Gómez, AG and Pisanty A (1995) Quantitative structure-activity relationships of competitive inhibitors of phosphoenolpyruvate carboxylase. Bioorg Med Chem. 3(3):217-25.

Matsumura, H, Xie, Y, Shirakata, S, Inoue, T, Yoshinaga, T, Ueno, Y, Izui, K and Kai Y. (2002) Crystal structures of C4 form maize and quaternary complex of *E. coli* phosphoenolpyruvate carboxylases. Structure 10(12):1721-30.

McFadden, HG, Harris, RLN and Jenkins, CLD (1989) Potential Inhibitors of Phosphoenolpyruvate Carboxylase. II. Phosphonic Acid Substrate Analogues Derived from Reaction of Trialkyl Phosphites with Halomethacrylates. Aust. J. Chem. 42:301-14.

Motti, CA, Bourne, D G, Burnell, JN, Doyle, JR, Haines, DS, Liptrot, CH, Llewellyn, LE, Ludke, S, Muirhead, A and Tapiolas DM (2007) Screening marine fungi for inhibitors of the C4 plant enzyme pyruvate phosphate dikinase: unguinol as a potential novel herbicide candidate. Appl Environ Microbiol. 73(6):1921-7.

Pairoba, CF, Colombo, SL and Andreo, CS (1996) Flavonoids as Inhibitors of NADP-Malic Enzyme and PEP Carboxylase from C4 Plants. Biosci. Biotech. Biochem. 60(5): 779-783.

Paulus, JK, Schlieper, D and Groth, G (2013a) Greater efficiency of photosynthetic carbon fixation due to single amino-acid substitution. Nature Communications 4: 1518.

Paulus, JK, Niehus, C and Groth, G (2013b) Evolution of C4 Phosphoenolpyruvate Carboxylase-enhanced feedback inhibitor tolerance is determined by a single residue. Mol. Plant 6: 1996-1999.

Trott, O and Olson, AJ (2010) AutoDock Vina: improving the speed and accuracy of docking with a new scoring function, efficient optimization and multithreading. Journal of Computational Chemistry 31:455-461.

Wallace, AC, Laskowski, RA and Thornton, 5M (1995) LIGPLOT: a program to generate schematic diagrams of protein-ligand interactions. Protein Eng. 8, 127-134.

Wolf, LK (2009) New software and Websites for the Chemical Enterprise, Chemical & Engineering News 87, 31.

The invention claimed is:

1. A method of using at least one compound, a salt or solvate thereof as a C4 plant selective herbicide, comprising applying said compound, salt or solvate to a plant, wherein binding of said compound to the malate binding site of aphosphoenolpyruvate carboxylase from a C3 plant is inhibited, and wherein said compound has a structure according to formula (I)

$$A\underset{\substack{(a) \\ X}}{\overset{}{\left(C(R^1)_n\right)}}_i C(R^2)_m \overset{(b)}{=\!=\!=} C(R^3)_p - B \quad (I)$$
$$\phantom{A\left(C(R^1)_n\right)_i} R^4 \phantom{=\!=} R^5$$

wherein A is wherein $R^6$, $R^7$, $R^8$, $R^9$ and $R^{10}$ are, independently of each other, selected from the group consisting of H, OH, carboxylic acid, ester, alkyl, alkoxy and halogen, or wherein two residues in ortho position to each other form a heterocyclic ring using —O—CH$_2$—O— or —O—CH$_2$—CH$_2$—O, and B is wherein $R^{11}$, $R^{12}$, $R^{13}$, $R^{14}$ and $R^{15}$ are, independently of each other, selected from the group consisting of H, OH, carboxylic acid, ester, alkyl, alkoxy and halogen, or wherein two residues in ortho position to each other form a heterocyclic ring using —O—CH$_2$—O— or —O—CH$_2$—CH$_2$—O—, and wherein $R^1$, $R^2$, $R^3$, $R^4$ and $R^5$ are, independently of each other H or an alkyl group, and wherein integer i is 0 or 1, and the bond (a) is a single or double bond, and wherein in case (a) is a double bond, n is 0 and X is O or S, and wherein in case (a) is a single bond n is 1, and X is H or an alkyl group, and wherein the bond (b) is a single or double bond, and wherein in case (b) is a double bond, m and p are 0, and wherein in case (b) is a single bond m and p are both 1, and wherein said compound being capable of binding to the malate binding site comprised by a phosphoenolpyruvate carboxylase from a C4 plant, thereby inhibiting said phosphoenolpyruvate carboxylase.

2. The method according to claim 1, wherein the compound has a structure according to formula (I) and wherein n is 0, (a) is a double bond, and X is O or S.

3. The method according to claim 2, wherein (b) is a double bond and X is O.

4. The method according to claim 2, wherein (b) is a single bond and X is O.

5. The method according to claim 1, wherein n is 1, (a) is a single bond, and X is H or alkyl.

6. The method according to claim 5, wherein (b) is a double bond.

7. The method according to claim 5, wherein b is a single bond.

8. The method of claim 1, wherein i is 1.

9. The method of claim 1, wherein the binding to the malate binding site of a phosphoenolpyruvate carboxylase from a C3 plant is inhibited by steric or electrostatic constraints of a conserved arginine in the binding site of the C3 phosphoenolpyruvate carboxylase.

10. The method of claim 9, wherein said arginine residue corresponds to Arg-884 in the C3 phosphoenolpyruvate carboxylase from *Flaveria pringlei*.

11. The method of claim 1, wherein at least one of $R^6$, $R^7$, $R^8$, $R^9$ or $R^{10}$ is OH.

12. The method of claim 2, wherein X is O.

13. The method of claim 12, wherein the compound has the structure wherein $R^6$, $R^7$, $R^8$, $R^9$, $R^{10}$, $R^{11}$, $R^{12}$, $R^{13}$, $R^{14}$ and $R^{15}$ are, independently of each other, selected from the group consisting of H, OH, carboxylic acid, ester, alkyl, alkoxy and halogen.

14. The method of claim 13, wherein at least one of $R^6$, $R^7$, $R^8$, $R^9$ or $R^{10}$ is OH.

* * * * *

SEQUENCE LISTING

<160> NUMBER OF SEQ ID NOS: 13

<210> SEQ ID NO 1
<211> LENGTH: 966
<212> TYPE: PRT
<213> ORGANISM: Flaveria trinervia

<400> SEQUENCE: 1

Met Ala Asn Arg Asn Val Glu Lys Leu Ala Ser Ile Asp Ala Gln Leu
1               5                   10                  15

Arg Leu Leu Val Pro Gly Lys Val Ser Glu Asp Asp Lys Leu Val Glu
            20                  25                  30

Tyr Asp Ala Leu Leu Leu Asp Lys Phe Leu Asp Ile Leu Gln Asp Leu
        35                  40                  45

His Gly Glu Asp Leu Lys Glu Ala Val Gln Gln Cys Tyr Glu Leu Ser
    50                  55                  60

Ala Glu Tyr Glu Gly Lys His Asp Pro Lys Lys Leu Glu Glu Leu Gly
65                  70                  75                  80

Ser Leu Leu Thr Ser Leu Asp Thr Gly Asp Ser Ile Val Ile Ala Lys
                85                  90                  95

Ala Phe Ser His Met Leu Asn Leu Ala Asn Leu Ala Glu Glu Leu Gln
            100                 105                 110

Ile Ala Tyr Arg Arg Ile Lys Leu Lys Ser Gly Asp Phe Ala Asp
            115                 120                 125

Glu Ala Asn Ala Thr Thr Glu Ser Asp Ile Glu Glu Thr Phe Lys Arg
    130                 135                 140

Leu Val His Lys Leu Asn Lys Ser Pro Glu Glu Val Phe Asp Ala Leu
145                 150                 155                 160

Lys Asn Gln Thr Val Glu Leu Val Leu Thr Ala His Pro Thr Gln Ser
                165                 170                 175

Val Arg Arg Ser Leu Leu Gln Lys His Gly Arg Ile Arg Asn Cys Leu
            180                 185                 190

Ala Gln Leu Tyr Ala Lys Asp Ile Thr Pro Asp Asp Lys Gln Glu Leu
        195                 200                 205

Asp Glu Ala Leu His Arg Glu Ile Gln Ala Ala Phe Arg Thr Asp Glu
    210                 215                 220

Ile Arg Arg Thr Pro Pro Thr Pro Gln Asp Glu Met Arg Ala Gly Met
225                 230                 235                 240

Ser Tyr Phe His Glu Thr Ile Trp Lys Gly Val Pro Lys Phe Leu Arg
                245                 250                 255

Arg Val Asp Thr Ala Leu Lys Asn Ile Gly Ile Asn Glu Arg Phe Pro
            260                 265                 270

Tyr Asn Ala Pro Leu Ile Gln Phe Ser Ser Trp Met Gly Gly Asp Arg
        275                 280                 285

Asp Gly Asn Pro Arg Val Thr Pro Glu Val Thr Arg Asp Val Cys Leu
    290                 295                 300

Leu Ala Arg Met Met Thr Ser Asn Met Tyr Phe Ser Gln Ile Glu Asp
305                 310                 315                 320

Leu Met Ile Glu Met Ser Met Trp Arg Cys Asn Ser Glu Leu Arg Val
                325                 330                 335

Arg Ala Glu Glu Leu Tyr Arg Thr Ala Arg Lys Asp Val Lys His Tyr
            340                 345                 350

```
Ile Glu Phe Trp Lys Arg Ile Pro Pro Asn Gln Pro Tyr Arg Val Ile
            355                 360                 365

Leu Gly Asp Val Arg Asp Lys Leu Tyr Asn Thr Arg Glu Arg Ser Arg
        370                 375                 380

His Leu Leu Val Asp Gly Lys Ser Asp Ile Pro Asp Glu Ala Val Tyr
385                 390                 395                 400

Thr Asn Val Glu Gln Leu Leu Glu Pro Leu Glu Leu Cys Tyr Arg Ser
                405                 410                 415

Leu Cys Asp Cys Gly Asp His Val Ile Ala Asp Gly Ser Leu Leu Asp
                420                 425                 430

Phe Leu Arg Gln Val Ser Thr Phe Gly Leu Ser Leu Val Lys Leu Asp
            435                 440                 445

Ile Arg Gln Glu Ser Asp Arg His Thr Glu Val Leu Asp Ala Ile Thr
        450                 455                 460

Gln His Leu Gly Ile Gly Ser Tyr Arg Glu Trp Ser Glu Glu Lys Arg
465                 470                 475                 480

Gln Glu Trp Leu Leu Ala Glu Leu Ser Gly Lys Arg Pro Leu Ile Gly
                485                 490                 495

Pro Asp Leu Pro Lys Thr Glu Glu Val Lys Asp Cys Leu Asp Thr Phe
            500                 505                 510

Lys Val Leu Ala Glu Leu Pro Ser Asp Cys Phe Gly Ala Tyr Ile Ile
        515                 520                 525

Ser Met Ala Thr Ser Thr Ser Asp Val Leu Ala Val Glu Leu Leu Gln
        530                 535                 540

Arg Glu Tyr His Ile Lys His Pro Leu Arg Val Val Pro Leu Phe Glu
545                 550                 555                 560

Lys Leu Ala Asp Leu Glu Ala Ala Pro Ala Ala Met Thr Arg Leu Phe
                565                 570                 575

Ser Met Asp Trp Tyr Arg Asn Arg Ile Asp Gly Lys Gln Glu Val Met
            580                 585                 590

Ile Gly Tyr Ser Asp Ser Gly Lys Asp Ala Gly Arg Phe Ser Ala Ala
        595                 600                 605

Trp Gln Leu Tyr Lys Thr Gln Glu Gln Ile Val Lys Ile Ala Lys Glu
610                 615                 620

Phe Gly Val Lys Leu Val Ile Phe His Gly Arg Gly Gly Thr Val Gly
625                 630                 635                 640

Arg Gly Gly Gly Pro Thr His Leu Ala Leu Leu Ser Gln Pro Pro Asp
                645                 650                 655

Thr Ile Asn Gly Ser Leu Arg Val Thr Val Gln Gly Glu Val Ile Glu
            660                 665                 670

Gln Ser Phe Gly Glu Glu His Leu Cys Phe Arg Thr Leu Gln Arg Phe
        675                 680                 685

Cys Ala Ala Thr Leu Glu His Gly Met Asn Pro Pro Ile Ser Pro Arg
        690                 695                 700

Pro Glu Trp Arg Glu Leu Met Asp Gln Met Ala Val Val Ala Thr Glu
705                 710                 715                 720

Glu Tyr Arg Ser Val Val Phe Lys Glu Pro Arg Phe Val Glu Tyr Phe
                725                 730                 735

Arg Leu Ala Thr Pro Glu Leu Glu Phe Gly Arg Met Asn Ile Gly Ser
                740                 745                 750

Arg Pro Ser Lys Arg Lys Pro Ser Gly Gly Ile Glu Ser Leu Arg Ala
            755                 760                 765

Ile Pro Trp Ile Phe Ser Trp Thr Gln Thr Arg Phe His Leu Pro Val
```

```
            770                 775                 780
Trp Leu Gly Phe Gly Ala Ala Phe Lys His Ala Ile Gln Lys Asp Ser
785                 790                 795                 800

Lys Asn Leu Gln Met Leu Gln Glu Met Tyr Lys Thr Trp Pro Phe Phe
                805                 810                 815

Arg Val Thr Ile Asp Leu Val Glu Met Val Phe Ala Lys Gly Asn Pro
                820                 825                 830

Gly Ile Ala Ala Leu Asn Asp Lys Leu Leu Val Ser Glu Asp Leu Arg
                835                 840                 845

Pro Phe Gly Glu Ser Leu Arg Ala Asn Tyr Glu Glu Thr Lys Asn Tyr
850                 855                 860

Leu Leu Lys Ile Ala Gly His Lys Asp Leu Leu Gly Asp Pro Tyr
865                 870                 875                 880

Leu Lys Gln Gly Ile Arg Leu Arg Asp Pro Tyr Ile Thr Thr Leu Asn
                885                 890                 895

Val Cys Gln Ala Tyr Thr Leu Lys Arg Ile Arg Asp Pro Asn Tyr His
                900                 905                 910

Val Thr Leu Arg Pro His Ile Ser Lys Glu Tyr Ala Ala Glu Pro Ser
                915                 920                 925

Lys Pro Ala Asp Glu Leu Ile His Leu Asn Pro Thr Ser Glu Tyr Ala
                930                 935                 940

Pro Gly Leu Glu Asp Thr Leu Ile Leu Thr Met Lys Gly Ile Ala Ala
945                 950                 955                 960

Gly Met Gln Asn Thr Gly
                965

<210> SEQ ID NO 2
<211> LENGTH: 966
<212> TYPE: PRT
<213> ORGANISM: Flaveria pringlei

<400> SEQUENCE: 2

Met Ala Asn Arg Asn Leu Glu Lys Leu Ala Ser Ile Asp Ala Gln Leu
1               5                   10                  15

Arg Leu Leu Val Pro Gly Lys Val Ser Glu Asp Lys Leu Ile Glu
                20                  25                  30

Tyr Asp Ala Leu Leu Leu Asp Lys Phe Leu Asp Ile Leu Gln Asp Leu
                35                  40                  45

His Gly Glu Asp Leu Lys Glu Ala Val Gln Glu Cys Tyr Glu Leu Ser
        50                  55                  60

Ala Glu Tyr Glu Gly Lys His Asp Pro Lys Lys Leu Glu Glu Leu Gly
65                  70                  75                  80

Ser Val Leu Thr Ser Leu Asp Pro Gly Asp Ser Ile Val Ile Ala Lys
                85                  90                  95

Ala Phe Ser His Met Leu Asn Leu Ala Asn Leu Ala Glu Glu Val Gln
                100                 105                 110

Ile Ala Tyr Arg Arg Arg Ile Lys Leu Lys Arg Gly Asp Phe Ala Asp
                115                 120                 125

Glu Ala Asn Ala Thr Thr Glu Ser Asp Ile Glu Glu Thr Phe Lys Lys
        130                 135                 140

Leu Val Leu Lys Leu Asn Lys Ser Pro Glu Glu Val Phe Asp Ala Leu
145                 150                 155                 160

Lys Asn Gln Thr Val Asp Leu Val Leu Thr Ala His Pro Thr Gln Ser
                165                 170                 175
```

```
Val Arg Arg Ser Leu Leu Gln Lys His Gly Arg Ile Arg Asn Cys Leu
            180                 185                 190

Ala Gln Leu Tyr Ala Lys Asp Ile Thr Pro Asp Lys Gln Glu Leu
        195                 200                 205

Asp Glu Ala Leu His Arg Glu Ile Gln Ala Ala Phe Arg Thr Asp Glu
        210                 215                 220

Ile Arg Arg Thr Pro Pro Thr Pro Gln Asp Glu Met Arg Ala Gly Met
225                 230                 235                 240

Ser Tyr Phe His Glu Thr Ile Trp Lys Gly Val Pro Lys Phe Leu Arg
                245                 250                 255

Arg Val Asp Thr Ala Leu Lys Asn Ile Gly Ile Asn Glu Arg Val Pro
            260                 265                 270

Tyr Asn Ala Pro Leu Ile Gln Phe Ser Ser Trp Met Gly Gly Asp Arg
        275                 280                 285

Asp Gly Asn Pro Arg Val Thr Pro Glu Val Thr Arg Asp Val Cys Leu
        290                 295                 300

Leu Ala Arg Met Met Ala Ser Asn Met Tyr Phe Ser Gln Ile Glu Asp
305                 310                 315                 320

Leu Met Phe Glu Met Ser Met Trp Arg Cys Asn Ser Glu Leu Arg Val
                325                 330                 335

Arg Ala Glu Glu Leu Tyr Arg Thr Ala Arg Arg Asp Val Lys His Tyr
            340                 345                 350

Ile Glu Phe Trp Lys Gln Val Pro Pro Thr Glu Pro Tyr Arg Val Ile
        355                 360                 365

Leu Gly Asp Val Arg Asp Lys Leu Tyr Asn Thr Arg Glu Arg Ser Arg
        370                 375                 380

His Leu Leu Ala His Gly Ile Ser Asp Ile Pro Glu Glu Ala Val Tyr
385                 390                 395                 400

Thr Asn Val Glu Gln Phe Leu Glu Pro Leu Glu Leu Cys Tyr Arg Ser
                405                 410                 415

Leu Cys Asp Cys Gly Asp Arg Val Ile Ala Asp Gly Ser Leu Leu Asp
            420                 425                 430

Phe Leu Arg Gln Val Ser Thr Phe Gly Leu Ser Leu Val Lys Leu Asp
        435                 440                 445

Ile Arg Gln Glu Ser Asp Arg His Thr Asp Val Leu Asp Ala Ile Thr
        450                 455                 460

Gln His Leu Glu Ile Gly Ser Tyr Arg Glu Trp Ser Glu Glu Lys Arg
465                 470                 475                 480

Gln Glu Trp Leu Leu Ala Glu Leu Ser Gly Lys Arg Pro Leu Phe Gly
                485                 490                 495

Ser Asp Leu Pro Lys Thr Glu Glu Val Lys Asp Val Leu Asp Thr Phe
            500                 505                 510

Asn Val Leu Ala Glu Leu Pro Ser Asp Cys Phe Gly Ala Tyr Ile Ile
        515                 520                 525

Ser Met Ala Thr Ser Pro Ser Asp Val Leu Ala Val Glu Leu Leu Gln
        530                 535                 540

Arg Glu Cys His Val Lys His Pro Leu Arg Val Val Pro Leu Phe Glu
545                 550                 555                 560

Lys Leu Ala Asp Leu Glu Ala Ala Pro Ala Met Ala Arg Leu Phe
                565                 570                 575

Ser Ile Asp Trp Tyr Arg Asn Arg Ile Asp Gly Lys Gln Glu Val Met
            580                 585                 590

Ile Gly Tyr Ser Asp Ser Gly Lys Asp Ala Gly Arg Phe Ser Ala Ala
```

```
                595                 600                 605
        Trp Gln Leu Tyr Lys Ala Gln Glu Ile Ile Lys Val Ala Lys Glu
        610                 615                 620

Phe Gly Val Lys Leu Val Ile Phe His Gly Arg Gly Thr Val Gly
        625                 630                 635                 640

Arg Gly Gly Gly Pro Thr His Leu Ala Ile Leu Ser Gln Pro Asp
                            645                 650                 655

Thr Ile His Gly Ser Leu Arg Val Thr Val Gln Gly Glu Val Ile Glu
                    660                 665                 670

Gln Ser Phe Gly Glu His Leu Cys Phe Arg Thr Leu Gln Arg Phe
                675                 680                 685

Cys Ala Ala Thr Leu Glu His Gly Met Asn Pro Pro Ile Ser Pro Arg
        690                 695                 700

Pro Glu Trp Arg Glu Leu Met Asp Gln Met Ala Val Val Ala Thr Glu
        705                 710                 715                 720

Glu Tyr Arg Ser Ile Val Phe Lys Glu Pro Arg Phe Val Glu Tyr Phe
                            725                 730                 735

Arg Leu Ala Thr Pro Glu Leu Glu Tyr Gly Arg Met Asn Ile Gly Ser
                    740                 745                 750

Arg Pro Ser Lys Arg Lys Pro Ser Gly Gly Ile Glu Ser Leu Arg Ala
                755                 760                 765

Ile Pro Trp Ile Phe Ala Trp Thr Gln Thr Arg Phe His Leu Pro Val
        770                 775                 780

Trp Leu Gly Phe Gly Ala Ala Phe Lys His Ala Ile Lys Lys Asp Ser
        785                 790                 795                 800

Lys Asn Leu Gln Met Leu Gln Glu Met Tyr Lys Thr Trp Pro Phe Phe
                            805                 810                 815

Arg Val Thr Ile Asp Leu Val Glu Met Val Phe Ala Lys Gly Asp Pro
                    820                 825                 830

Gly Ile Ala Ala Leu Asn Asp Lys Leu Leu Val Ser Glu Asp Leu Trp
                835                 840                 845

Pro Phe Gly Glu Ser Leu Arg Ala Asn Tyr Glu Glu Thr Lys Asp Tyr
        850                 855                 860

Leu Leu Lys Ile Ala Gly His Arg Asp Leu Leu Glu Gly Asp Pro Tyr
        865                 870                 875                 880

Leu Lys Gln Arg Ile Arg Leu Arg Asp Ser Tyr Ile Thr Thr Leu Asn
                            885                 890                 895

Val Cys Gln Ala Tyr Thr Leu Lys Arg Ile Arg Asp Pro Asn Tyr His
                    900                 905                 910

Val Thr Leu Arg Pro His Ile Ser Lys Glu Tyr Ala Ala Glu Pro Ser
                915                 920                 925

Lys Pro Ala Asp Glu Leu Ile His Leu Asn Pro Thr Ser Glu Tyr Ala
        930                 935                 940

Pro Gly Leu Glu Asp Thr Leu Ile Leu Thr Met Lys Gly Ile Ala Ala
        945                 950                 955                 960

Gly Met Gln Asn Thr Gly
                            965

<210> SEQ ID NO 3
<211> LENGTH: 33
<212> TYPE: PRT
<213> ORGANISM: Hordeum vulgare

<400> SEQUENCE: 3
```

-continued

Pro Tyr Leu Lys Gln Arg Leu Arg Leu Arg Asp Pro Tyr Ile Thr Thr
1               5                   10                  15

Leu Asn Val Cys Gln Ala Tyr Thr Leu Lys Arg Ile Arg Asp Pro Ser
            20                  25                  30

Phe

<210> SEQ ID NO 4
<211> LENGTH: 33
<212> TYPE: PRT
<213> ORGANISM: Oryza sativa ssp. indica

<400> SEQUENCE: 4

Leu Tyr Leu Lys Gln Arg Leu Arg Leu Arg Asn Ala Tyr Ile Thr Thr
1               5                   10                  15

Leu Asn Val Cys Gln Ala Tyr Thr Met Lys Arg Ile Arg Asp Pro Asp
            20                  25                  30

Tyr

<210> SEQ ID NO 5
<211> LENGTH: 33
<212> TYPE: PRT
<213> ORGANISM: Triticum aestivum

<400> SEQUENCE: 5

Pro Tyr Leu Lys Gln Arg Leu Arg Leu Arg Asp Ala Tyr Ile Thr Thr
1               5                   10                  15

Met Asn Val Cys Gln Ala Tyr Thr Leu Lys Arg Ile Arg Asp Pro Asp
            20                  25                  30

Tyr

<210> SEQ ID NO 6
<211> LENGTH: 33
<212> TYPE: PRT
<213> ORGANISM: Arabidopsis thaliana

<400> SEQUENCE: 6

Pro Tyr Leu Lys Gln Arg Leu Arg Leu Arg Asp Ser Tyr Ile Thr Thr
1               5                   10                  15

Leu Asn Val Cys Gln Ala Tyr Thr Leu Lys Arg Ile Arg Asp Ala Asn
            20                  25                  30

Tyr

<210> SEQ ID NO 7
<211> LENGTH: 33
<212> TYPE: PRT
<213> ORGANISM: Flaveria pringlei

<400> SEQUENCE: 7

Pro Tyr Leu Lys Gln Arg Ile Arg Leu Arg Asp Ser Tyr Ile Thr Thr
1               5                   10                  15

Leu Asn Val Cys Gln Ala Tyr Thr Leu Lys Arg Ile Arg Asp Pro Asn
            20                  25                  30

Tyr

<210> SEQ ID NO 8
<211> LENGTH: 33
<212> TYPE: PRT
<213> ORGANISM: Flaveria trinervia

<400> SEQUENCE: 8

```
Pro Tyr Leu Lys Gln Gly Ile Arg Leu Arg Asp Pro Tyr Ile Thr Thr
1               5                   10                  15

Leu Asn Val Cys Gln Ala Tyr Thr Leu Lys Arg Ile Arg Asp Pro Asn
            20                  25                  30

Tyr

<210> SEQ ID NO 9
<211> LENGTH: 33
<212> TYPE: PRT
<213> ORGANISM: Flaveria australasica

<400> SEQUENCE: 9

Pro Tyr Leu Lys Gln Gly Ile Arg Leu Arg Asp Pro Tyr Ile Thr Thr
1               5                   10                  15

Leu Asn Val Cys Gln Ala Tyr Thr Leu Lys Arg Ile Arg Asp Pro Asn
            20                  25                  30

Tyr

<210> SEQ ID NO 10
<211> LENGTH: 33
<212> TYPE: PRT
<213> ORGANISM: Zea mays

<400> SEQUENCE: 10

Pro Phe Leu Lys Gln Gly Leu Val Leu Arg Asn Pro Tyr Ile Thr Thr
1               5                   10                  15

Leu Asn Val Phe Gln Ala Tyr Thr Leu Lys Arg Ile Arg Asp Pro Asn
            20                  25                  30

Phe

<210> SEQ ID NO 11
<211> LENGTH: 33
<212> TYPE: PRT
<213> ORGANISM: Sorghum bicolor

<400> SEQUENCE: 11

Pro Tyr Leu Lys Gln Gly Leu Arg Leu Arg Asn Pro Tyr Ile Thr Thr
1               5                   10                  15

Leu Asn Val Phe Gln Ala Tyr Thr Leu Lys Arg Ile Arg Asp Pro Ser
            20                  25                  30

Phe

<210> SEQ ID NO 12
<211> LENGTH: 33
<212> TYPE: PRT
<213> ORGANISM: Saccharum spontaneum

<400> SEQUENCE: 12

Pro Tyr Leu Lys Gln Gly Leu Arg Leu Arg Asn Pro Tyr Ile Thr Thr
1               5                   10                  15

Leu Asn Val Leu Gln Ala Tyr Thr Leu Lys Arg Ile Arg Asp Pro Ser
            20                  25                  30

Phe

<210> SEQ ID NO 13
<211> LENGTH: 33
<212> TYPE: PRT
<213> ORGANISM: Saccharum officinarum
```

```
<400> SEQUENCE: 13

Pro Tyr Leu Lys Gln Gly Leu Arg Leu Arg Asn Pro Tyr Ile Thr Thr
1               5                   10                  15

Leu Asn Val Leu Gln Ala Tyr Thr Leu Lys Arg Ile Arg Asp Pro Cys
            20                  25                  30

Phe
```